(12) United States Patent
Dobrinsky et al.

(10) Patent No.: US 10,166,307 B2
(45) Date of Patent: Jan. 1, 2019

(54) ADHESIVE DEVICE WITH ULTRAVIOLET ELEMENT

(71) Applicant: Sensor Electronic Technology, Inc., Columbia, SC (US)

(72) Inventors: Alexander Dobrinsky, Loudonville, NY (US); Michael Shur, Latham, NY (US); Remigijus Gaska, Columbia, SC (US)

(73) Assignee: Sensor Electronic Technology, Inc., Columbia, SC (US)

( * ) Notice: Subject to any disclaimer, the term of this patent is extended or adjusted under 35 U.S.C. 154(b) by 358 days.

(21) Appl. No.: 14/925,060

(22) Filed: Oct. 28, 2015

(65) Prior Publication Data
US 2016/0114186 A1    Apr. 28, 2016

Related U.S. Application Data

(60) Provisional application No. 62/069,486, filed on Oct. 28, 2014, provisional application No. 62/072,724, filed on Oct. 30, 2014.

(51) Int. Cl.
*A61L 2/10*     (2006.01)
*A61N 5/06*     (2006.01)
(Continued)

(52) U.S. Cl.
CPC .............. *A61L 2/10* (2013.01); *A61B 5/0071* (2013.01); *A61F 13/0246* (2013.01); *A61N 5/0624* (2013.01); *G01N 21/4738* (2013.01); *G01N 21/6486* (2013.01); *A61L 2202/14* (2013.01); *A61N 2005/0645* (2013.01); *A61N 2005/0651* (2013.01); *A61N 2005/0654* (2013.01); *A61N 2005/0661* (2013.01);
(Continued)

(58) Field of Classification Search
CPC .......... A61N 5/0624; A61N 2005/0645; A61N 2005/0661; A61N 2005/0666; A61L 2/10; A51F 13/0246
See application file for complete search history.

(56) References Cited

U.S. PATENT DOCUMENTS 5,094,955 A    3/1992    Calandra et al.
5,902,552 A    5/1999    Brickley
(Continued)

FOREIGN PATENT DOCUMENTS

CN    1531449 A    9/2004
CN    2695025 Y    4/2005
(Continued)

OTHER PUBLICATIONS

Han, I., International Application No. PCT/US/2015/057729, International Search Report and Written Opinion, dated Feb. 15, 2016, 12 pages.
(Continued)

*Primary Examiner* — Nathan J Jenness
(74) *Attorney, Agent, or Firm* — LaBatt, LLC

(57) ABSTRACT

An adhesive device with an ultraviolet element is disclosed. The adhesive device with an ultraviolet element can be used to provide a treatment of a surface of an object. The treatment can include cleaning, disinfection, sterilization and sanitization. The adhesive device with an ultraviolet element can also be used as a self-adhesive bandage.

20 Claims, 13 Drawing Sheets

(51) Int. Cl.
*A61F 13/02* (2006.01)
*G01N 21/47* (2006.01)
*G01N 21/64* (2006.01)
*A61B 5/00* (2006.01)

(52) U.S. Cl.
CPC .......... *A61N 2005/0666* (2013.01); *G01N 2201/0221* (2013.01); *G01N 2201/062* (2013.01); *G01N 2201/0621* (2013.01)

(56) References Cited

U.S. PATENT DOCUMENTS

| | | | |
|---|---|---|---|
| 5,968,445 A | 10/1999 | McCarville et al. | |
| 6,272,768 B1 | 8/2001 | Danese | |
| 7,459,694 B2 | 12/2008 | Scheir et al. | |
| 7,553,456 B2 | 6/2009 | Gaska et al. | |
| 7,626,187 B2 | 12/2009 | Younts | |
| 7,634,996 B2 | 12/2009 | Gaska et al. | |
| 8,226,887 B2 | 7/2012 | Harmon et al. | |
| 8,277,734 B2 | 10/2012 | Koudymov et al. | |
| 8,372,128 B2 | 2/2013 | Reuben | |
| 8,980,178 B2 | 3/2015 | Gaska et al. | |
| 9,006,680 B2 | 4/2015 | Bettles et al. | |
| 9,138,499 B2 | 9/2015 | Bettles et al. | |
| 2003/0031586 A1* | 2/2003 | Eckhardt | A61L 2/10 422/24 |
| 2004/0147984 A1* | 7/2004 | Altshuler | A46B 15/0036 607/88 |
| 2005/0080465 A1* | 4/2005 | Zelickson | A61N 5/0616 607/88 |
| 2005/0267451 A1* | 12/2005 | Black | A61C 15/02 606/13 |
| 2006/0167532 A1 | 7/2006 | Parker | |
| 2006/0173514 A1 | 8/2006 | Biel et al. | |
| 2007/0205382 A1 | 9/2007 | Gaska et al. | |
| 2007/0233208 A1 | 10/2007 | Kurtz et al. | |
| 2008/0058907 A1* | 3/2008 | Reuben | A61F 13/0203 607/91 |
| 2011/0073838 A1 | 3/2011 | Khan et al. | |
| 2011/0243789 A1 | 10/2011 | Roberts | |
| 2011/0309032 A1 | 12/2011 | Makl | |
| 2012/0165716 A1 | 6/2012 | Reuben | |
| 2013/0035629 A1 | 2/2013 | Soltz et al. | |
| 2013/0048545 A1 | 2/2013 | Shatalov et al. | |
| 2013/0048876 A1 | 2/2013 | Crawford | |
| 2013/0270445 A1 | 10/2013 | Gaska et al. | |
| 2014/0060094 A1 | 3/2014 | Shur et al. | |
| 2014/0060095 A1 | 3/2014 | Shur et al. | |
| 2014/0060096 A1 | 3/2014 | Shur et al. | |
| 2014/0060104 A1 | 3/2014 | Shur et al. | |
| 2014/0061509 A1 | 3/2014 | Shur et al. | |
| 2014/0105784 A1 | 4/2014 | Smeeton et al. | |
| 2014/0202962 A1 | 7/2014 | Bilenko et al. | |
| 2014/0222116 A1 | 8/2014 | Pierce | |
| 2014/0264076 A1 | 9/2014 | Bettles et al. | |
| 2015/0008167 A1 | 1/2015 | Shturm et al. | |
| 2015/0069270 A1 | 3/2015 | Shur et al. | |
| 2015/0165079 A1 | 6/2015 | Shur et al. | |
| 2015/0217011 A1 | 8/2015 | Bettles et al. | |
| 2015/0297767 A1 | 10/2015 | Gaska et al. | |
| 2015/0336810 A1 | 11/2015 | Smetona et al. | |
| 2016/0000953 A1 | 1/2016 | Bettles et al. | |
| 2016/0058020 A1 | 3/2016 | Shur et al. | |
| 2016/0074547 A1 | 3/2016 | Dobrinsky et al. | |
| 2016/0074548 A1 | 3/2016 | Dobrinsky et al. | |
| 2016/0077278 A1 | 3/2016 | Dobrinsky et al. | |
| 2016/0077292 A1 | 3/2016 | Dobrinsky et al. | |
| 2016/0088868 A1 | 3/2016 | Dobrinsky et al. | |
| 2016/0106873 A1 | 4/2016 | Dobrinsky et al. | |
| 2016/0114067 A1 | 4/2016 | Dobrinsky et al. | |
| 2016/0128526 A1 | 5/2016 | Dobrinsky et al. | |

FOREIGN PATENT DOCUMENTS

| | | | |
|---|---|---|---|
| CN | 103416874 A | 12/2013 | |
| CN | 103445335 A | 12/2013 | |
| CN | 103656871 A | 3/2014 | |
| CN | 104114136 A | 10/2014 | |
| JP | 2008539808 A | 11/2008 | |

OTHER PUBLICATIONS

Green, Y., U.S. Appl. No. 14/925,068, Notice of Allowance, dated Nov. 15, 2016, 23 pages.
Han, I., International Application No. PCT/US/2015/057730, International Search Report and Written Opinion, dated Feb. 5, 2016, 12 pages.
Green, Y., U.S. Appl. No. 15/469,683, Office Action1, dated Mar. 27, 2018, 35 pages.
Chinese patent office, Application No. 201580059439.4, Office Action, dated Oct. 23, 2018, 10 pages. (There is no English translation available).
Chinese patent office, Application No.201580059960.8, Office Action, dated Oct. 23, 2018, 11 pages. (There is no English translation available).

* cited by examiner

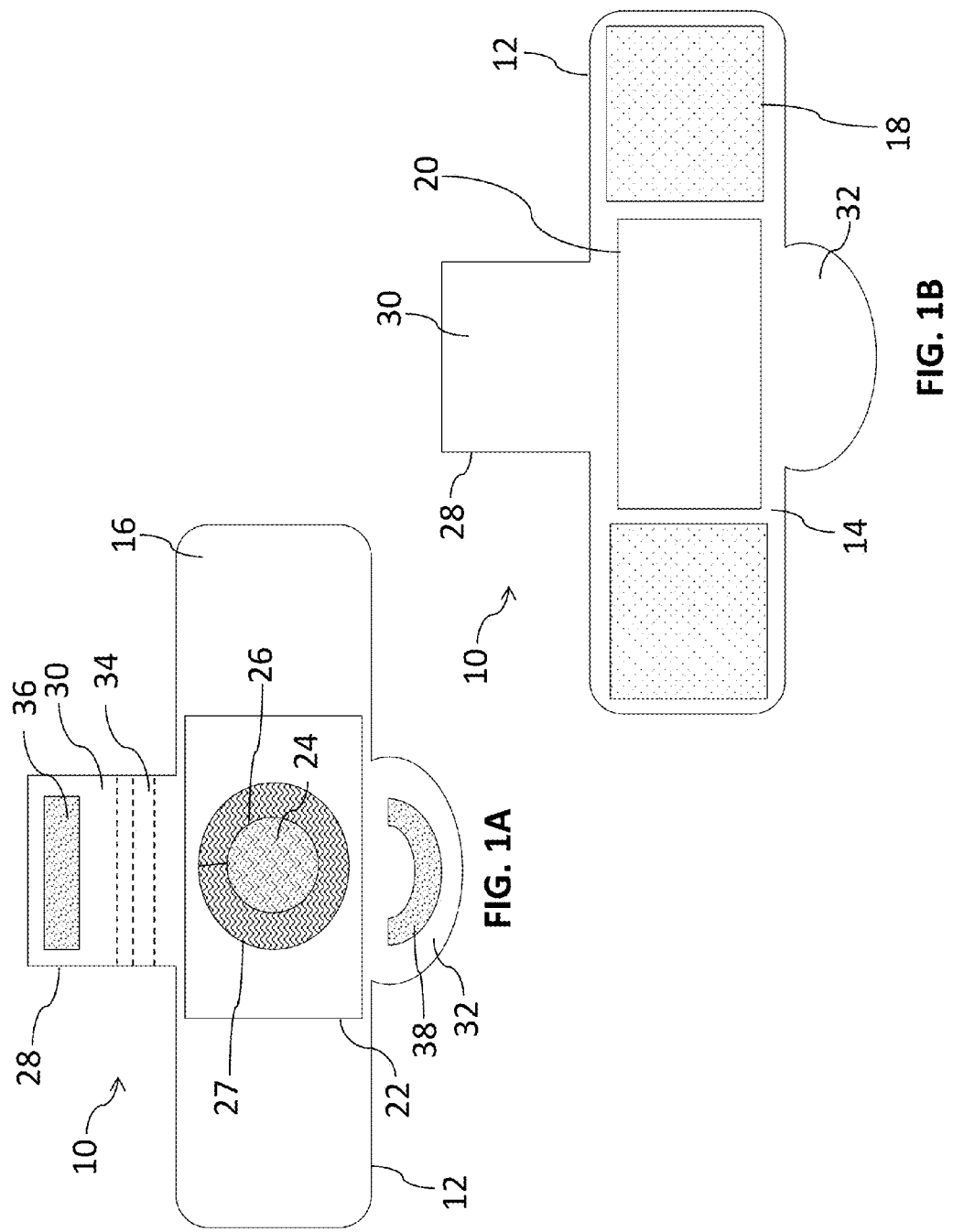

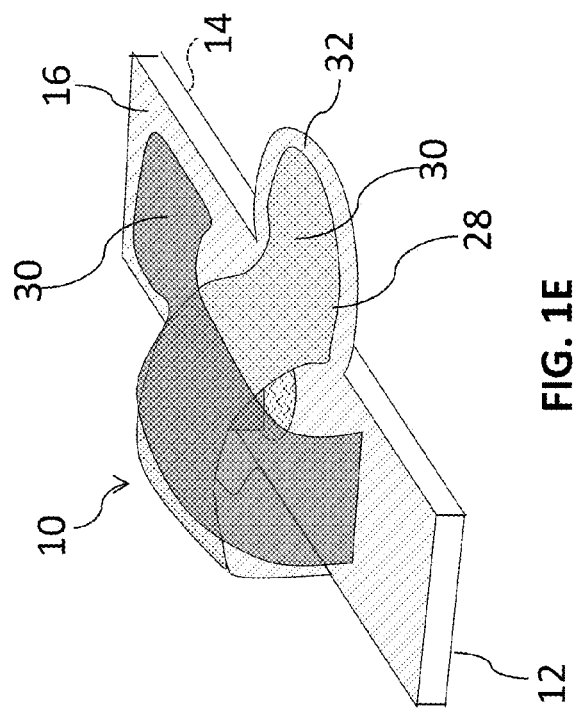
FIG. 1C
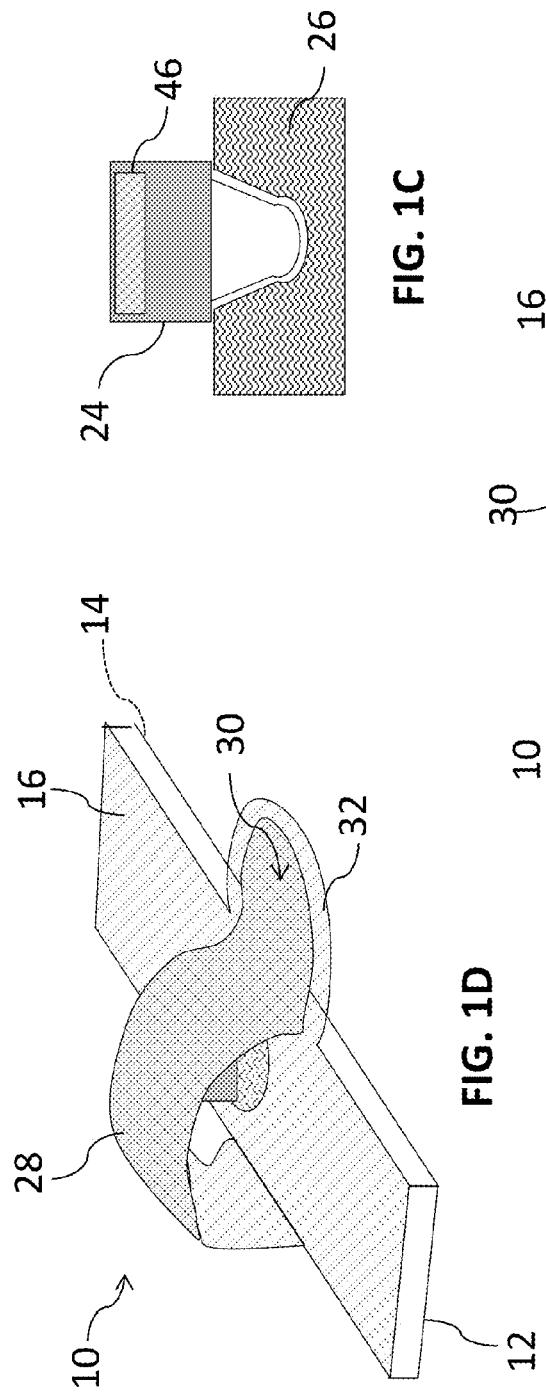
FIG. 1D
FIG. 1E

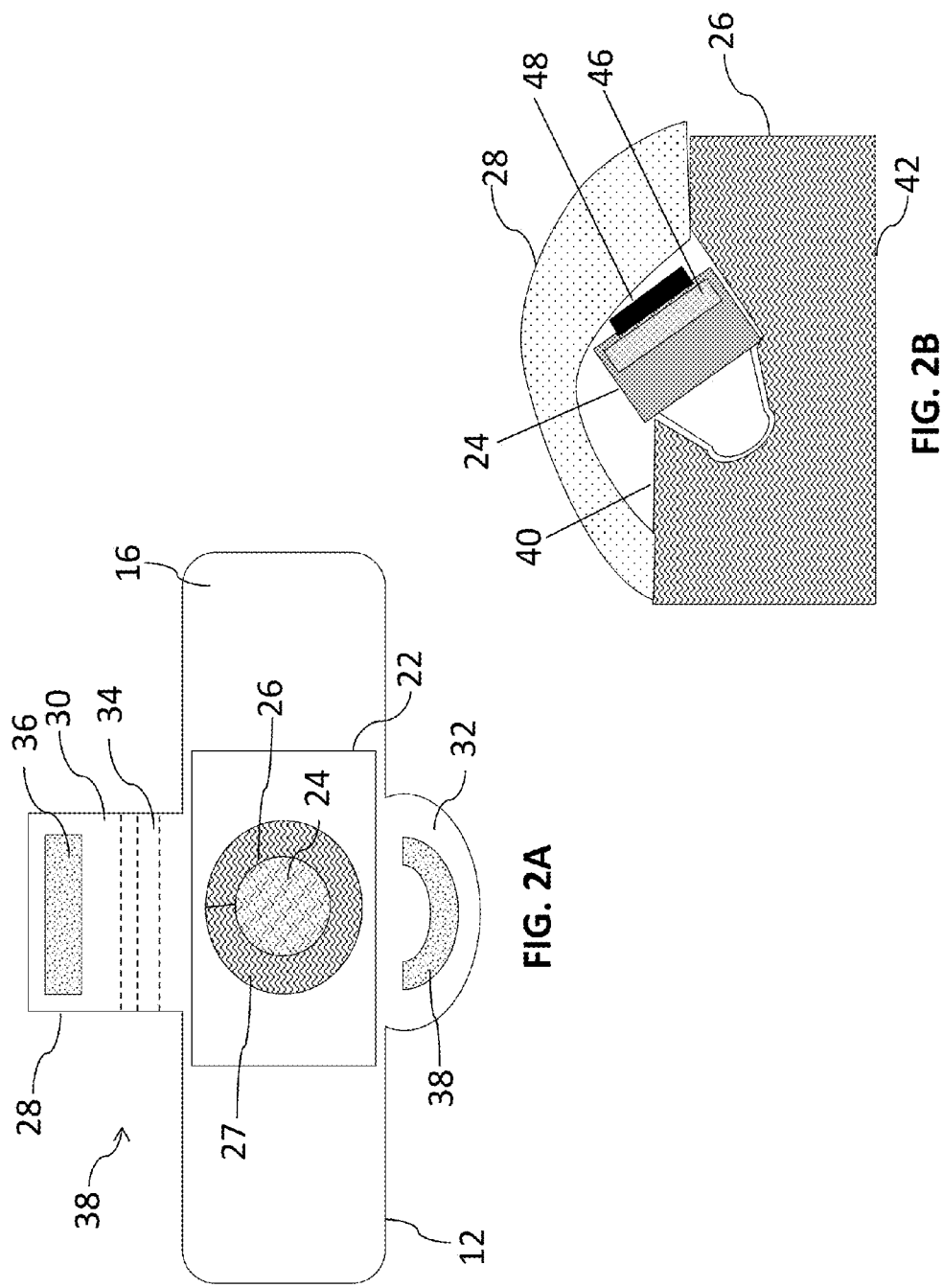

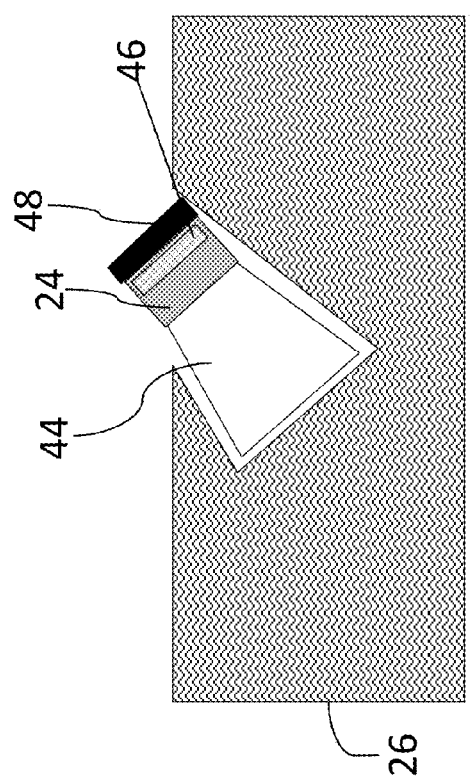
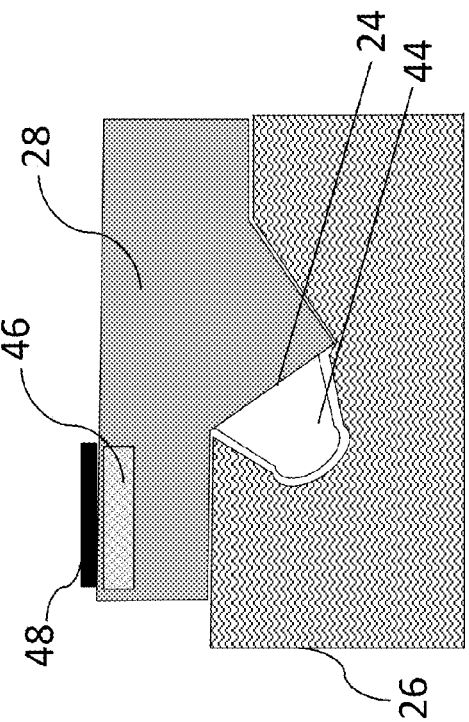
FIG. 2C
FIG. 2D

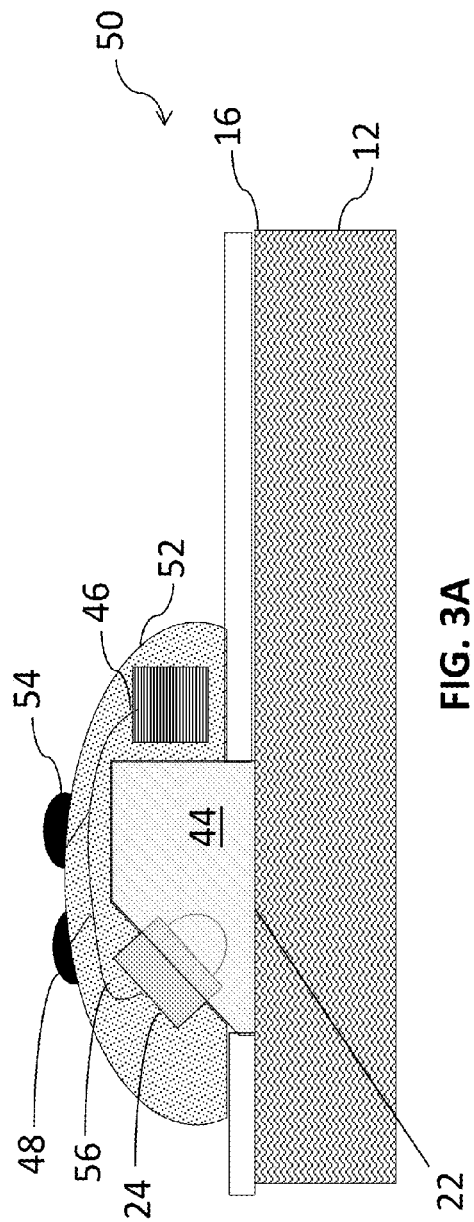
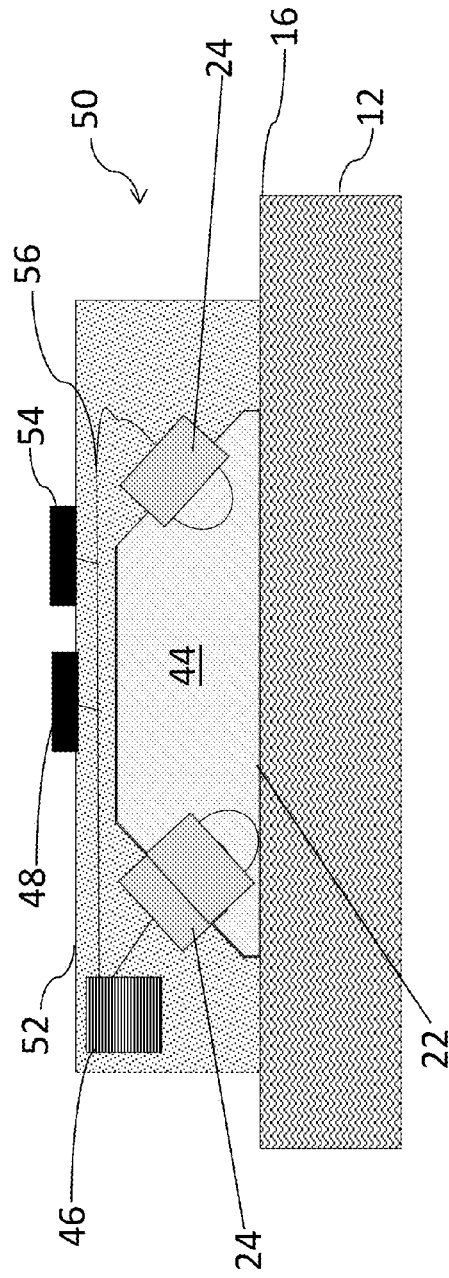
FIG. 3A
FIG. 3B

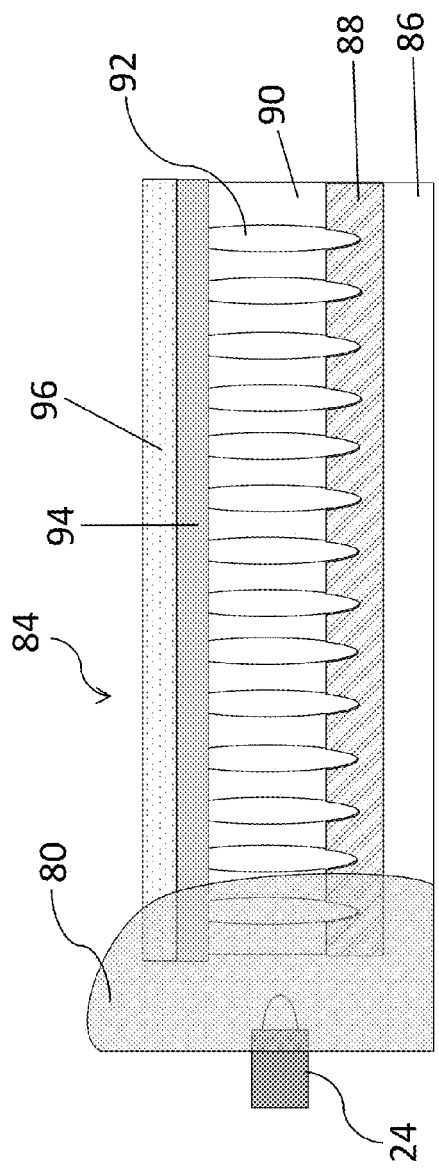
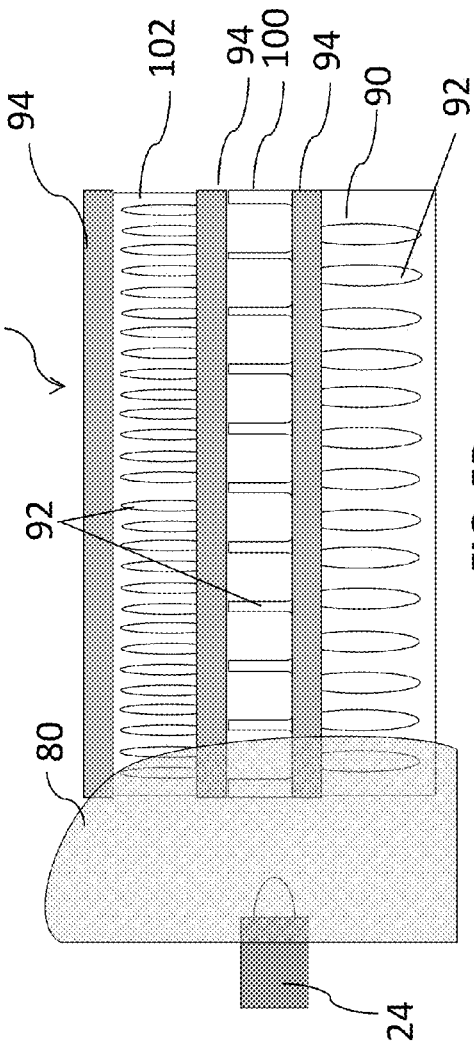

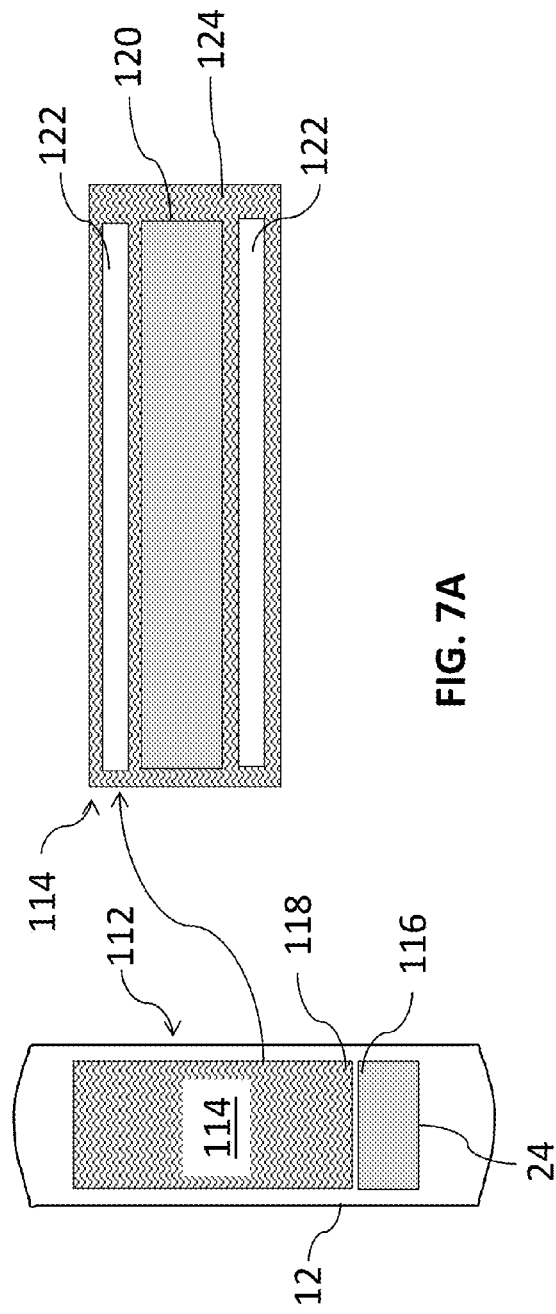
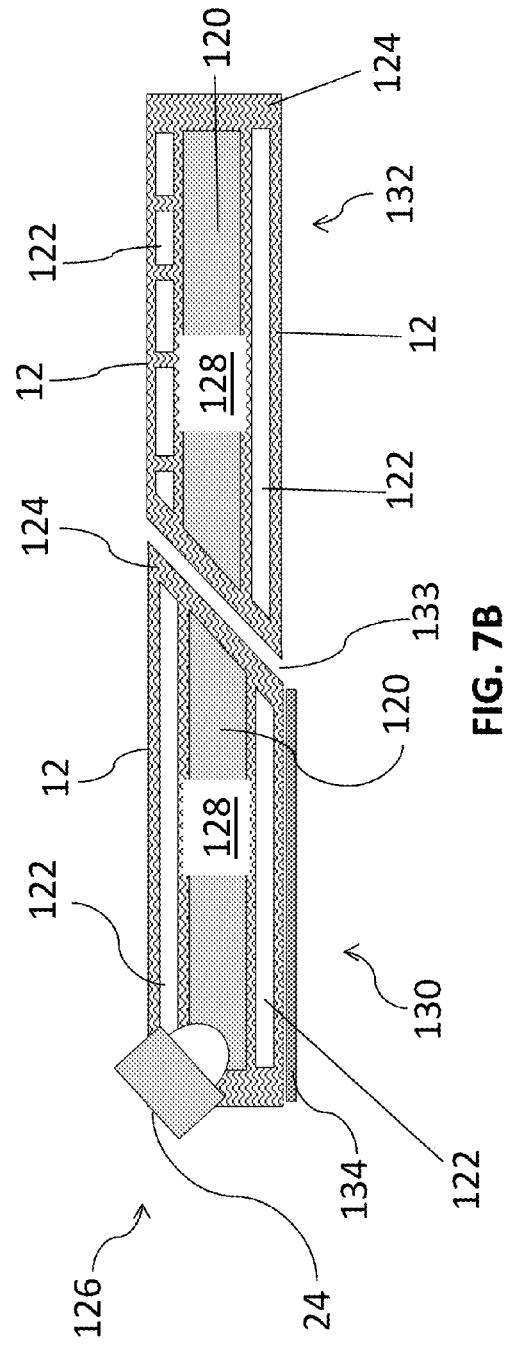
FIG. 7A
FIG. 7B

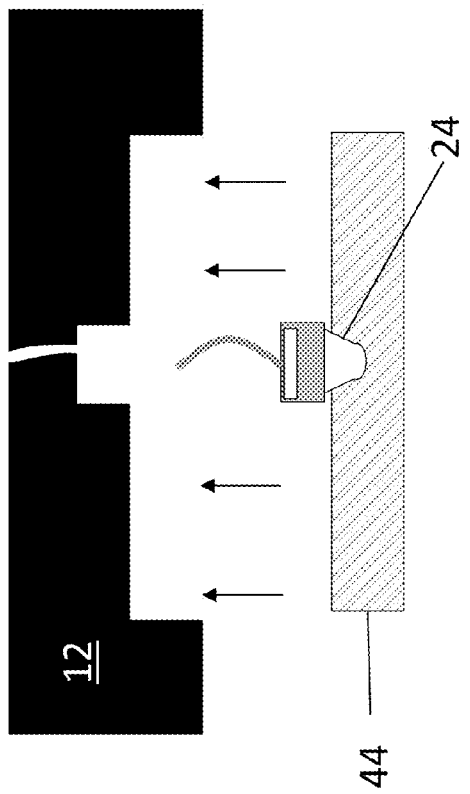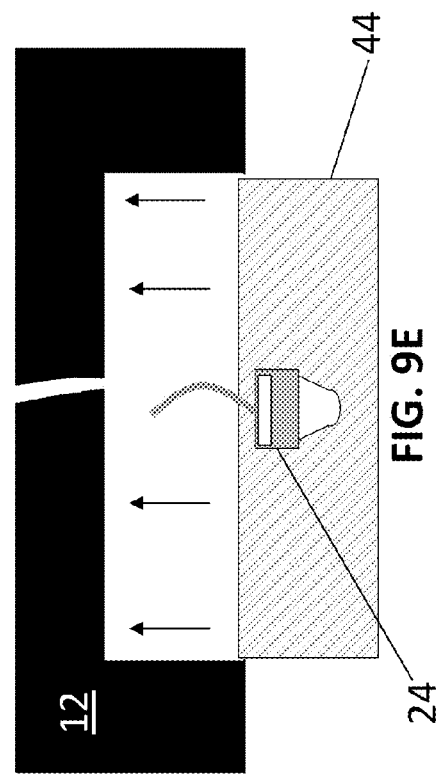

ADHESIVE DEVICE WITH ULTRAVIOLET ELEMENT

REFERENCE TO RELATED APPLICATIONS

The current patent application claims the benefit of U.S. Provisional Application No. 62/069,486, which was filed on 28 Oct. 2014; and U.S. Provisional Application No. 62/072,724, which was filed on 30 Oct. 2014, each of which is incorporated herein by reference in its entirety.

TECHNICAL FIELD

The disclosure relates generally to treatment of surfaces using ultraviolet radiation, and more particularly, to an adhesive device for treatment of an object, which can include cleaning, sterilizing, disinfecting, and/or sanitizing a surface of the object.

BACKGROUND ART

A self-adhesive bandage having an absorbent pad that is sanitized by light infused photodynamically is one example of an adhesive device used for disinfection. This self-adhesive bandage can employ a light emitting diode, a side emitting fiber optic mesh, or a light emitting diode chip array embedded in an outer surface of a transmissive perforated non-stick thin film absorbent pad. The light emitting diodes are powered by a battery sealed in the bandage. Irradiation is controlled by a preprogrammed timing algorithm chip embedded in the bandage and electronically initiated by peeling the backing from the self-adhesive bandage. A drawback associated with this self-adhesive bandage is that the side emitting design of the fiber optic mesh or the light emitting diode chip array is unlikely to produce sufficiently uniform distribution of ultraviolet radiation. This sacrifices the efficiency of the ultraviolet radiation and can consequently impair the disinfection provided by this self-adhesive bandage.

SUMMARY OF THE INVENTION

Aspects of the present invention provide an adhesive device using ultraviolet radiation for the treatment of an object.

A first aspect of the invention provides a device comprising: a substrate having a first side and a second side; an adhesive layer formed on the first side of the substrate that is configured to adhere to an object; an ultraviolet transparent region formed on the first side of the substrate without overlapping with the adhesive layer, wherein the ultraviolet transparent region is configured for placement adjacent to a surface of the object that is subject to undergo treatment upon the adhesive layer adhering to the object; an ultraviolet transparent window formed on the second side of the substrate; and an ultraviolet radiation source, coupled to the second side of the substrate, that is configured to emit ultraviolet radiation through the ultraviolet transparent window towards the ultraviolet transparent region and onto the surface of the subject.

A second aspect of the invention provides an adhesive treatment device, comprising: a substrate having a first side and a second side with an ultraviolet transparent region embedded in a volume of the substrate between the first side and the second side, wherein the ultraviolet transparent region has a surface portion that is adjacent to an ambient at the first side of the substrate; an adhesive layer formed on the first side of the substrate that is configured to adhere to an object; an ultraviolet radiation source coupled to the second side of the substrate that is configured to emit ultraviolet radiation through the ultraviolet transparent region towards the ambient at the first side of the substrate and onto a surface of the subject that is to undergo treatment; and a fastener configured to fasten the ultraviolet radiation source to the substrate.

A third aspect of the invention provides a self-adhesive treatment device, comprising: a substrate having a first side and a second side; an adhesive layer formed on the first side of the substrate that is configured to adhere to an object; an opening formed in the second side of the substrate; and an ultraviolet treatment system disposed in the opening that is configured to treat a surface of the object, wherein the ultraviolet treatment system comprises an ultraviolet radiation source that is configured to emit ultraviolet radiation onto the surface of the subject.

The illustrative aspects of the present invention are designed to solve one or more of the problems herein described and/or one or more other problems not discussed.

BRIEF DESCRIPTION OF THE DRAWINGS

These and other features of the disclosure will be more readily understood from the following detailed description of the various aspects of the present invention taken in conjunction with the accompanying drawings that depict various aspects of the invention.

FIGS. 1A-1E show an illustrative adhesive treatment device according to an embodiment of the present invention;

FIGS. 2A-2D show an illustrative adhesive treatment device according to another embodiment of the present invention;

FIGS. 3A-3B show an illustrative adhesive treatment device according to another embodiment of the present invention;

FIGS. 5A-5B show illustrative light guiding layers according to embodiments of the present invention that are suitable for use with the adhesive treatment devices described herein;

FIGS. 7A-7B show illustrative adhesive treatment devices according to another embodiment of the present invention;

FIGS. 9A-9E show illustrative embodiments showing how an ultraviolet radiation source can be implemented with a flexible substrate in an adhesive treatment device according to another embodiment of the present invention.

It is noted that the drawings may not be to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

Figure 4:
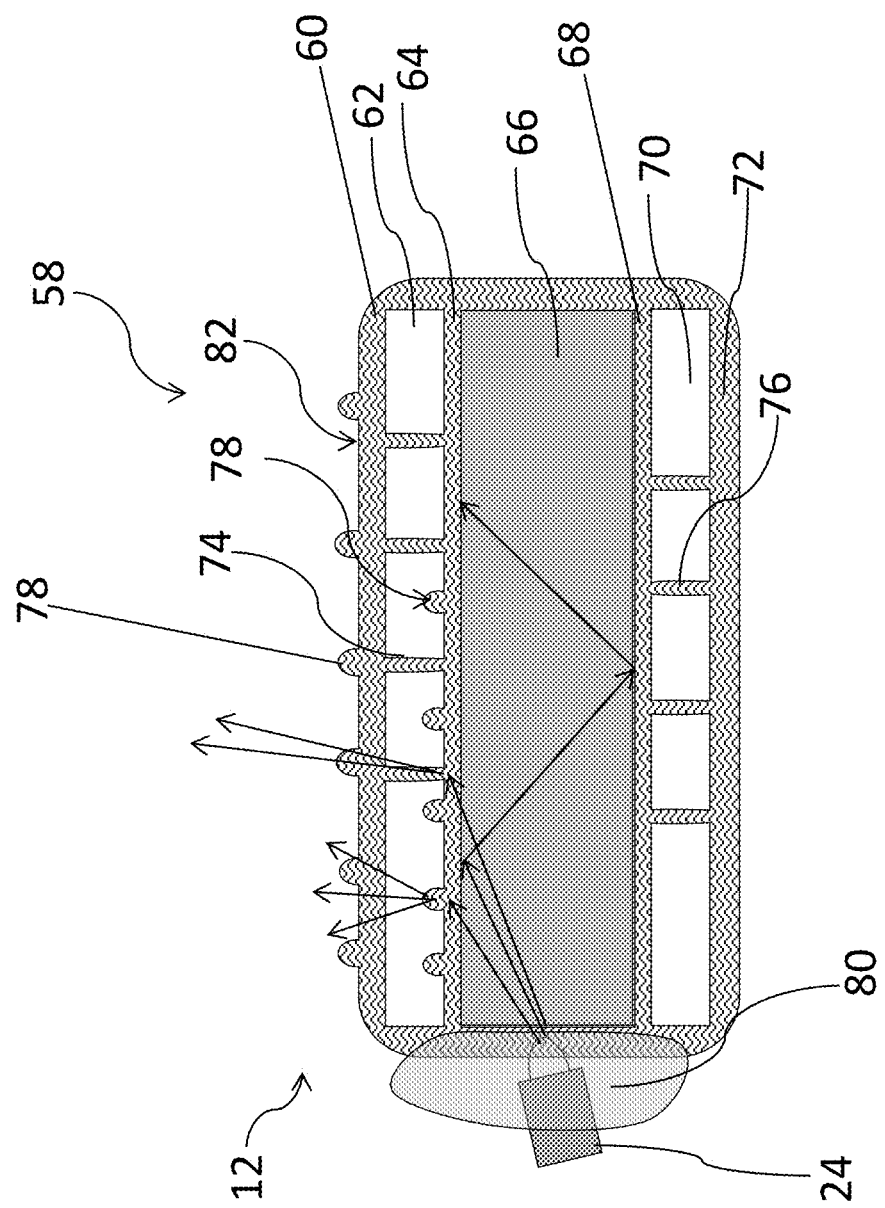
FIG. 4 shows an illustrative light guiding layer according to an embodiment of the present invention that is suitable for use with the adhesive treatment devices described herein.

As indicated above, aspects of the present invention are directed to an adhesive treatment device that uses ultraviolet radiation to provide treatment to an object. As used herein, treatment can entail cleaning, disinfecting, sterilizing, and/or sanitizing a surface of an object. Cleaning generally means the removal of visible soil (e.g., organic and inorganic material) from objects and surfaces. Disinfecting generally means destroying pathogenic and other types of microorganisms, while sterilizing is more extensive in that it kills all microbial forms. Sanitizing generally means reducing the number of bacterial contaminants to a predetermined safe level. As used herein, an object can include any item or article that varies in shape and size, and which has a surface that an adhesive can be adhered thereto. Although the various embodiments of the present invention described herein are with reference to using an adhesive treatment device to disinfect or sterilize a skin wound on a digit or extremity of a person, it is understood that this is only one example in which an adhesive treatment device described herein can be used, and is not meant to limit the scope of the present invention. Furthermore, those skilled in the art will appreciate that the adhesive treatment device used to treat a surface of an object as described herein can include any now known or later developed approach that incorporates the concepts of the various embodiments of the present invention.

Ultraviolet radiation, which can be used interchangeably with ultraviolet light, means electromagnetic radiation having a wavelength ranging from approximately 10 nanometers (nm) to approximately 400 nm. Within this range, there is ultraviolet-A (UV-A) electromagnetic radiation having a wavelength ranging from approximately 315 nm to approximately 400 nm, ultraviolet-B (UV-B) electromagnetic radiation having a wavelength ranging from approximately 280 nm to approximately 315 nm, and ultraviolet-C (UV-C) electromagnetic radiation having a wavelength ranging from approximately 100 nm to approximately 280 nm.

As used herein, a layer, a film, or a material is transparent when it allows at least ten percent of radiation having a target wavelength, which is radiated at a normal incidence to an interface of the layer, film or material, to pass there through. Furthermore, as used herein, a reflective layer, film or material is reflective when it reflects at least ten percent of radiation having a target wavelength, which is radiated at a normal incidence to an interface of the layer, film or material. The target wavelength of the radiation can correspond to a wavelength of radiation emitted or sensed (e.g., peak wavelength+/−five nanometers) by an active region of an optoelectronic device during operation thereof. For a given layer, the wavelength can be measured in a material of consideration and can depend on a refractive index of the material.

Turning to the drawings, FIGS. 1A-1E show varying views of an illustrative adhesive treatment device 10 according to an embodiment of the present invention. As shown in FIGS. 1A, 1B, 1D and 1E, the device includes a substrate 12 having a first side 14 and a second side 16. In one embodiment, the substrate 12 is flexible in that can bend or flex its shape and size without impairing its ability to perform its intended function. In one embodiment, as shown in FIG. 1B, an adhesive layer 18 can be formed on the first side 14 of the substrate 12 that is configured to adhere to an object. An ultraviolet transparent region 20 having an ultraviolet transparent active layer can also be formed on the first side 14 of the substrate 12 without overlapping with the adhesive layer 18.

The ultraviolet transparent region 20 is configured for placement immediately adjacent to a surface of the object that is targeted to undergo a treatment upon the adhesive layer 18 adhering to the object. It is understood that the size, the amount, and the location of the adhesive layer 18 and the ultraviolet transparent region 20 on the first side 14 of the substrate 12 as shown in FIG. 1B is only illustrative of one configuration and those skilled in the art will recognize that there are various configurations in which an adhesive layer and an ultraviolet transparent region can be formed on a substrate and are within the scope of the various embodiments of the present invention.

In one embodiment, as shown in FIG. 1A, an ultraviolet transparent window 22 is formed on the second side 16 of the substrate 12. An ultraviolet radiation source 24 can be coupled to the second side 16 of the substrate 12. In this manner, the ultraviolet radiation source 24 is configured to emit ultraviolet radiation through the ultraviolet transparent window 22 towards the ultraviolet transparent region 20 and onto the surface of a subject that is to undergo a treatment with the device 10.

In one embodiment, the substrate 12 can be formed from material that includes, but is not limited to, a woven fabric and/or an elastic material that are suitable for use as a bandage. It is understood that the material can have an adhesive that enables adhesion to a person's skin on an area outside a wound. That is, the material can have at least some areal domains that are adhesive. In an embodiment, some or all of the substrate 12 and/or ultraviolet transparent region 20 can be formed of a flexible substrate as shown and described in U.S. Provisional Application No. 62/072,724, which was filed on 30 Oct. 2014, and which is hereby incorporated by reference.

In one embodiment, portions or the entire substrate 12, as well as the ultraviolet transparent region 20, and the ultraviolet transparent window 22 can include any ultraviolet transparent material such as an ultraviolet transparent fluoropolymer or waveguides formed from such a polymer. Examples of an ultraviolet transparent fluoropolymer that are suitable for use with the substrate 12, the ultraviolet transparent region 20, and the ultraviolet transparent window 22 can include, but are not limited to, fluorinated ethylene-propylene (EFEP), fluorinated ethylene propylene (FEP), perfluoroalkoxy (PFA), tetrafluoroethylene hexafluoropropylene vinylidene fluoride (THV), polytetrafluoroethylene (PTFE), polyvinylidene fluoride (PVDF), ethylene-tetrafluoroethylene (ETFE), ethylene chlorotrifluoroethylene (ECTFE), polychlorotrifluoroethene (PCTFE), a copolymer of tetrafluoroethylene and perfluoro methyl alkoxy (MFA), low density polyethylene (LDPE), perfluoroether (PFA), and/or the like, and/or the like. Other examples of material that can be used in the substrate 12 including the ultraviolet transparent region 20, and the ultraviolet transparent window 22, to waveguide, transmit and diffuse ultraviolet radiation can also include fused silica, sapphire, quartz, anodized aluminum oxide (AAO), polylactide (PLA), and fluoride based materials such as calcium fluoride ($CaF_2$) or magnesium fluoride ($MgF_2$), and/or the like.

In one embodiment, the adhesive layer 18 can be formed from material that includes, but is not limited to, a woven fabric or an elastic material with an adhesive thereon, such as a material typically used in bandages.

The ultraviolet radiation source 24 can comprise any combination of one or more ultraviolet radiation emitters to form an ultraviolet treatment system. Examples of ultraviolet radiation emitters can include, but are not limited to, high intensity ultraviolet lamps (e.g., high intensity mercury lamps), discharge lamps, ultraviolet light emitting diodes (LEDs), super luminescent LEDs, laser diodes, and/or the like. In one embodiment, the ultraviolet radiation source 24 can include a set of LEDs manufactured with one or more layers of materials selected from the group-III nitride material system (e.g., $Al_xIn_yGa_{1-x-y}N$, where $0 \geq x$, $y \geq 1$, and $x+y \geq 1$ and/or alloys thereof).

In one embodiment, the ultraviolet radiation source 24 can be formed or coupled to the substrate 12 in any of multiple of different arrangements. For example, the ultraviolet radiation source 24 can be monolithically embedded into the substrate 12 either through an opening on the first side of the substrate 12, or by incorporating the ultraviolet radiation source 24 inside the substrate 12.

In one embodiment, as shown in FIGS. 1A and 1C, the ultraviolet radiation source 24 can be attached to the substrate via a coupling port 26 that is located on the second side 16 in an opening or cavity 27 of the substrate 12 located above the ultraviolet transparent window 22. The coupling port 26 can comprise a cavity formed to allow a tight insertion of an LED, with the cavity having ultraviolet transparent walls that are configured to accommodate placement of the ultraviolet radiation source 24 as well as removal therefrom. In this manner, the coupling port 26 can propagate ultraviolet radiation emitted from the ultraviolet radiation source 24 through the ultraviolet transparent window 22 towards the ultraviolet transparent region 20 located on the first side 14 of the substrate 12 and onto the surface of the object that is subject to treatment by the device 10.

It is understood that the coupling port 26 can be configured to couple other sources to the adhesive treatment device 10 to complement the treatment of a particular object. For example, it may be desirable to use other sources such as a visible source, an infrared source, a heating source, a vibrational source, a medical treatment source, chemical treatment sources, and/or the like. Use of such sources will depend on the object that is to receive treatment and the particular type of treatment that is desired.

FIGS. 1A, 1B, 1D and 1E show an example of a fastener 28 that can be used to further secure the ultraviolet radiation source 24 within the coupling port 26. In one embodiment, the fastener 28 can comprise at least one adhesive strap 30 attached to either the first side 14 and/or the second side 16 of the substrate 12 that is configured to extend over the ultraviolet radiation source 24 and secure it in place upon fastening to an attachable region 32 that is part of the substrate 12. The adhesive strap 30 can comprise a folding region 34 that enables the adhesive strap 30 to extend over the ultraviolet radiation source 24 and be secured to the attachable region 32. In one embodiment, the adhesive strap 30 can comprise an adhesive region 36 that can adhere to a complementary adhesive region 38 located on the attachable region 32 of the substrate 12. It is understood that the fastener 28 and the attachable region 32 of the substrate 12 can be coupled together by means other than common adhesion. For example, a hook and loop fastener can be used in adhesive regions 36 and 38. A non-exhaustive list of other forms of attachment that can be used at regions 36 and 38 can include magnets, suction cups, static electricity, and/or the like.

FIG. 1E shows a configuration in which two adhesive straps 30 can be used to secure the ultraviolet radiation source 24 within the coupling port 26. In one embodiment, the adhesive straps 30 are oriented substantially perpendicular to each other. In this manner, each strap 30 can be extended over the ultraviolet radiation source 24 in different directions that are substantially orthogonal to each other to effectuate a further secure fit within the coupling port 26. Those skilled in the art will appreciate that the material and length used for the adhesive strap(s) 30 will depend on the size of the substrate 12 and the ultraviolet radiation source 24, as well as the object that is subjected to the treatment provided by the device 10. Selection of such parameters is well within the purview of those skilled in the art.

In one embodiment, the adhesive treatment device 10 can take the form of a self-adhesive bandage that can be used to provide treatment to a skin wound that includes cleaning, disinfection, sterilization, and/or sanitization. In this scenario, the first side 14 of the substrate 12 can be the part of the bandage that is attached to the skin wound, while the second side 16 of the substrate 12 having the ultraviolet radiation source 24 is situated away from the wound. In this manner, the ultraviolet transparent region 20 and the ultraviolet transparent window 22 are situated over the skin wound in order to direct ultraviolet radiation emitted from the ultraviolet radiation source 24 and onto the surface of the wound.

In this embodiment of a self-adhesive bandage, the first side 14 of the substrate 12 can include a wound sanitizing absorbing mesh deposited on an area of the ultraviolet transparent region 20. In this manner, the wound sanitizing absorbing mesh can be applied adjacent to the skin wound such that the mesh touches the wound and delivers a sanitizing action. In one embodiment, the wound sanitizing absorbing mesh can be configured with antibacterial chemicals and/or medicinal ointment such as antibiotic jelly or the like, to provide treatment to the skin wound that acts in conjunction with the ultraviolet radiation source 14. In another embodiment, the ultraviolet transparent region 20 can include a photo-activated disinfection layer that works in conjunction with the ultraviolet radiation source 24 and the wound sanitizing absorbing mesh to complement treatment of a skin wound. The photo-activated disinfection layer can include, but is not limited to, a titanium oxide ($TiO_2$) layer, a copper layer, a carbon layer, or any other layer having sterilizing properties under ultraviolet radiation.

In one embodiment, the coupling port 26 can be configured to include a medicine administering port in addition to the port that is used to accommodate the ultraviolet radiation source 24. In this manner, the medicine administering port can be used to deliver medicine and/or fluids to the wound and/or remove fluids therefrom. It is understood that such a medicine administering port can be part of the coupling port 26 or even a distinct element that is located on the substrate 12 in the opening 27 apart from the coupling port 26, or even in another opening formed on the second side 16 of the substrate 12.

In the embodiment in which the adhesive treatment device 10 is used as a self-adhesive bandage, the first side 14 of the substrate 12 can also include a removable protective pad that is disposed over the first side 14 of the substrate 12 covering the adhesive layer 18 and the ultraviolet transparent region 20, wherein removal of the protective pad from the first side 14 of the substrate 12 exposes the adhesive layer 18 and the ultraviolet transparent region 20 for application to the surface of the object. In this manner, the ultraviolet radiation source 24 in conjunction with the ultraviolet transparent window 22 and the ultraviolet transparent region 20, can be activated and ready to apply treatment once the adhesive layer 18 is applied to the wound. Prior to removal, the protective pad can serve to protect the first side 14 of the substrate 12 while the device is in a storage mode and not in use. In one embodiment, the protective pad can include a film of material such as a polyethelene film or fluoropolymer film.

In an embodiment where the self-adhesive bandage uses a coupling port 26 to accommodate the ultraviolet radiation source 24, those skilled in the art will appreciate that it is possible to remove the ultraviolet radiation source 24 from the port 26 and reuse it in another bandage having a coupling port. Otherwise, reusing the ultraviolet radiation source 24 with other bandages having the radiation source embedded in the substrate 12 would be difficult.

In another embodiment, the adhesive treatment device 10 can take the form of a self-adhesive bandage that can be used to provide treatment to a medical device surface that is in need of a treatment, where such treatment can include cleaning, disinfection, sterilization, and/or sanitization. In this scenario, the ultraviolet transparent region 20 can include an adhesive that is applied, adhered, or wrapped, etc., about a surface of a medical device. In this manner, the ultraviolet radiation source 24 can perform a treatment of the surface of the medical device.

FIGS. 2A-2D show an illustrative adhesive treatment device 38 according to an embodiment of the present invention. In particular, FIGS. 2A-2D show that the adhesive treatment device 38 can be configured similar to the adhesive treatment device 10 of FIGS. 1A-1E, except that FIGS. 2A-2D show that the treatment device 38 can utilize ultraviolet radiation sources that differ in shape and function. In addition, each of the ultraviolet radiation sources can be placed in an opening of the coupling port 26 at a predetermined orientation angle permitting each to emit the ultraviolet radiation through the substrate 12 and the ultraviolet transparent region 20 and out to ambient at a target angle.

FIG. 2B shows the ultraviolet radiation source 24 can be inserted in the coupling port 26 at an angle to a source-to-port interface 40 which is parallel to a substrate-to-surface interface 42 and secured by the fastener 28. This type of coupling with the ultraviolet radiation source 24 can promote waveguiding, by allowing the majority of light emitted from the source to undergo total internal reflection at the interface between the waveguide and surrounding ambient (typically being air). In this case, the interface between the waveguide and surrounding ambient can be the substrate-to-surface interface 42.

FIG. 2C shows that the ultraviolet radiation source 24 can include an optical element 44 in addition to being inserted in the coupling port 26 at a predetermined orientation angle. Examples of an optical element 44 that are suitable for use with the ultraviolet radiation source 24 include, but are not limited to, a lens, a prism, a pyramid, a truncated pyramid and a light guiding layer. The optical element 44 can be selected to be highly effective at collimating the ultraviolet radiation. For example, as shown in FIG. 2C, the optical element 44 can include a truncated cone having an outer diameter larger than the diameter adjacent to the surface of the ultraviolet radiation source 24. In another embodiment, the optical element 44 can be a lens, or a truncated cone, or even comprise a reflector for collimation, or otherwise, for controlling angular distribution of the ultraviolet light.

FIG. 2D shows the ultraviolet radiation source 24 also with an optical element 44 that is secured firmly underneath the fastener 28. This contrasts with the illustration FIG. 2B where the fastener 28 is used to loosely secure the ultraviolet radiation source 24 within the coupling port 26. It is understood that the degree of fastening the fastener 28 will depend on the application of the adhesive treatment device 38 and the position in which it is used during application. For example, if the adhesive treatment device 38 is used as bandage and it is applied in a position where the ultraviolet radiation source could become dislodged, then one may want to apply the fastener 28 around the ultraviolet radiation source 24 more firmly. Use of the adhesive treatment device 38 in more commercial or industrial applications may or may not require such a firm application of the fastener 28.

FIGS. 2B-2D show that the ultraviolet radiation source 24 can include a control module 46 having a power unit. FIGS. 2B-2C show that the control module 46 can be incorporated with the ultraviolet radiation source 24, while FIG. 2D shows that the control module can be a separate module operatively coupled to the ultraviolet radiation source 24 either by a wire or through a wireless communication assuming that the ultraviolet radiation source 24 contains a module for capturing and processing such wireless inputs. For example, FIG. 2D shows the control module 46 integrated with the fastener 28.

In operation, the control module 46 can be used to operate in cooperation with the ultraviolet radiation source 24. In one embodiment, the control module 46 can control at least one of a plurality of predetermined ultraviolet radiation characteristics associated with the ultraviolet radiation emitted from the ultraviolet radiation source 24. The predetermined ultraviolet radiation characteristics that can be controlled by the control module 46 can include wavelengths, intensities, spatial distribution of the ultraviolet radiation and durations of a treatment and/or the like. In one embodiment, the control module 46 can control the wavelength of ultraviolet radiation and the intensity in a particular treatment. As an example, the control module 46 can control the ultraviolet radiation source 24 to operate at a target wavelength and intensity for a duration that is designed for the disinfection of bacteria and/or viruses that may exist on a surface such as, for example, a skin wound. During this time, the control module can control the ultraviolet radiation source 24 to operate at a different target wavelength and intensity for a specified duration that is designed for a treatment. In another example, the ultraviolet radiation source 24 can be used to deliver an optimal distribution of intensity, while the time schedule of the ultraviolet radiation source 24 can be tailored to deliver an appropriate dose for treatment such as for example, a disinfection. To this extent, the dose can be calculated once the intensity distribution is known. In one embodiment, the intensity distribution can be either modeled or experimentally tested for a typical or a set of typical surfaces that require treatment. Those skilled in the art will readily appreciate that there are many possibilities in how the control module can control the ultraviolet radiation source 24.

The control module 46 can also be configured to receive condition signals representative of certain operational parameters from sensors that may be used with the adhesive treatment device 38. A non-exhaustive list of sensors that may be used in conjunction with the adhesive treatment device 38 can include a temperature sensor, heart rate sensor, a moisture sensor, a humidity sensor, a bacterial fluorescent sensor, a chemical sensor, and a radiation sensor. It is understood that such sensors could be located on the substrate 12 or the object itself that is to undergo a treatment and communicate with the control module 46 for example, via a wireless or wired connection.

Upon receiving any condition signals from the sensor, the control module 46 can turn on or off the ultraviolet radiation source 24 dependent upon the detected conditions, attaining a predetermined dosing, finishing a specified dosing time duration, and/or the like. Likewise, the control module 46 can adjust one or more of the ultraviolet radiation characteristics based on the detected conditions. For example, the control module 46 can adjust the intensity, the wavelength, the duration and or the pattern of the ultraviolet radiation emitted from the ultraviolet radiation source 24. In another example, the control module 46 can cause the ultraviolet radiation source 24 to switch from radiating in the UV-C range, which is optimal for germicidal (e.g., disinfection) purposes, to radiating in the UV-B range, which is optimal for certain medical treatment.

The control module 46 can include a timer with switches and/or the like to manage the duration that the ultraviolet radiation source 24 is on for a particular treatment. For example, the control module 46 operating in conjunction with the timer can manage the amount of time that the ultraviolet radiation source 24 radiates in the UV-C range versus the UV-B range. The duration and frequency treatment that the ultraviolet radiation source 24 is utilized can depend on detected condition signals as well as any other predetermined treatment factors that are pertinent to treating the object, including following a set predefined treatment schedule for a particular treatment of an object.

The control module 46 can also include a wireless transmitter and receiver that is configured to communicate with a remote location via any wireless communications solution, such as WiFi, BLUETOOTH, and/or the like. As used herein, a remote location is a location that is apart from the adhesive treatment system 38. For example, a remote computer can be used to transmit operational instructions to the wireless transmitter and receiver. The operational instructions can be used to program functions performed and managed by the control module 46 (e.g., controlling ultraviolet radiation source characteristics, doses, time schedule, intensity distribution, and/or the like). In another embodiment, the wireless transmitter and receiver can transmit treatment results (e.g., the detection of bacterial fluorescence, detection of bacterial contamination based on the detected fluorescence), data from any of the various sensors to the remote computer, to facilitate maintenance and diagnostic operations on the adhesive treatment system 38, turning on and/or off the ultraviolet radiation source 24 based on reported ultraviolet dosing information provided by the sensors, etc.

The power unit of the control module 46 can be configured to power the ultraviolet radiation source 24, the control module and any sensors via an electrical system. In one embodiment, the power unit can take the form of batteries or other power supply components, such as, for example, mechanically activated power generators like a vibration power generator based on magnetic inducted oscillations or stresses developed on a piezoelectric crystal, a super capacitor that is rechargeable, electrical accumulating elements charged by mechanical motion, a mechanical energy to electrical energy converter such as a piezoelectric crystal, solar elements. The various embodiments of the present invention are not limited to using only one particular power supply modality. For example, a vibration power generator can be used to generate power while a set of batteries can be used to store the power generated from the vibration power generator.

In another embodiment, the power unit can be a rechargeable device that works in conjunction with the control module 46. For example, a vibration power generator can be configured with rechargeable componentry. In another example, a wired or wireless charging system can be used as power options. For example, a wireless charging system can be used to charge a vibration power generator from an electromagnetic signal. In yet another example, a charge can be provided by the use of a piezoelectric crystal that functions according to mechanical pressure. The type of power supply and the particular treatment that is performed are factors that can determine how often a recharging operation is needed. For example, a typical LED, operating at 20 milliamperes (mA), with a coin battery rated 225 milliampere hour (mAH), can operate in a continuous mode for about 10 hours. A typical disinfection treatment session may last on the order of 10 minutes, thus resulting in approximately 60 disinfection sessions for the adhesive treatment device 38 (or for the ultraviolet radiation source 24) before the battery would need to be recharged or changed. For an extended life in this scenario, two or more coin batteries can be employed within the adhesive treatment device 38.

Referring back to FIGS. 2A-2D, the adhesive treatment device 38 can further include a user input system 48 that can initiate and terminate treatment of an object by the adhesive treatment device 38. As shown in FIGS. 2A-2D, the user input system 48 can be coupled to the ultraviolet radiation source 24. In one embodiment, the user input system 48 can comprise a button, a switch, or the like that can be depressed to indicate a series of requested actions. For example, consider a scenario in which the user input system 48 is a button. In this case, the button can be used to input a set of parameters for operation of the ultraviolet radiation source 24, e.g., through a set of "clicks", wherein the click is defined as a way to depress and release the button, with clicks being either fast or slow. That is, fast clicks can comprise depressing the button followed by releasing the button, whereas slow clicks can comprise depressing the button, and holding the button in depressed mode for some measurable duration of time, such as a second, followed by releasing the button. It is understood that the clicks can be characterized as long or short instead of fast or slow and be used in the same manner. Those skilled in the art will appreciate that more than one button can be used to each input a desired action that can initiate an action with the ultraviolet radiation source 24 and/or the control module 46.

FIGS. 3A-3B show cross-sectional views of an adhesive treatment device 50 according to another embodiment. In particular, the adhesive treatment device 50 shown in FIGS. 3A-3B illustrates alternative configurations for the ultraviolet radiation source 24, the optical element 44, the control module 46 and the user input system 48. In particular, FIG. 3A shows a user input/output protrusion 52 coupled to the second side 16 of the substrate 12. In one embodiment, the user input/output protrusion 52 can enclose the ultraviolet radiation source 24, the optical element 44, the ultraviolet transparent window 22 and the control module 46. The user input system 48 and an operational indicator 54, which can provide an indication of the operation of the ultraviolet radiation source 24 and the status of the treatment, can be placed on the exterior of the user input/output protrusion 52.

In another embodiment, the operational indicator 54 can provide an indication of the fluorescence detected while performing a treatment. U.S. Provisional Application No. 62/066,459, which was filed on 21 Oct. 2014 and U.S. patent application Ser. No. 14/883,804, which was filed on 15 Oct. 2015, both of which are hereby incorporated by reference, provide further details of a visible and/or fluorescent feedback system. The user input system 48 and the operational indicator 54 can connect with the ultraviolet radiation source 24 and the control module 46 via a wired connection 56.

FIG. 3A also shows that the optical element 44 can comprise a prism that can be used to improve the coupling of the ultraviolet radiation source 24 with the ultraviolet transparent window 22 along with the user input/output protrusion 52 which can be formed from a transparent material described herein (e.g., a fluoropolymer).

FIG. 3B shows that the user input/output protrusion 52 can have a different shape than the more rounded protrusion illustrated in FIG. 3A. As shown in FIG. 3B, the user input/output protrusion 52 can include a rectangular shape. It is understood that the shape of the user input/output protrusion 52 as illustrated in FIGS. 3A-3B is not meant to be limiting as other shapes are suitable for use with the adhesive treatment device 50. FIG. 3B also shows that more than one ultraviolet radiation source 24 with the optical element 44, which can be a prism, can be used. It is understood that the number of ultraviolet radiation sources 24 in use with the adhesive treatment device 50 as illustrated in FIGS. 3A-3B is not meant to be limiting.

The user input/output protrusion 52 of FIGS. 3A-3B can also serve as a capping layer to the ultraviolet radiation source(s) 24. In this manner, the user input/output protrusion 52 can be used to prevent leakage of ultraviolet radiation from the second side of the substrate. In one embodiment, the user input/output protrusion 52 can be coated with ultraviolet reflective films including, but not limited to a fluoropolymer film, an aluminum film, a multilayer polymer film that includes a reflective polymer (e.g., Teflon), a multilayer polymer film that includes an aluminum film, a diffusively reflective material, such as a highly ultraviolet reflective expanded polytetrafluoroethylene (ePTFE) membrane (e.g., GORE® Diffuse Reflector Material), and/or the like, to prevent the escape of ultraviolet radiation from the ultraviolet radiation source 24. These same materials could also be applied to the second side 16 of the substrate 12 to prevent leakage.

FIG. 4 shows an illustrative light guiding layer 58 according to an embodiment of the present invention that is suitable for use with any of the adhesive treatment devices described herein. In one embodiment as indicated in FIG. 4, the substrate 12 of the adhesive treatment device can include the light guiding layer 58. In this manner, the light guiding layer 58 can utilize total internal reflection (TIR) to propagate the light there through to deliver the light to the surface of the object that is to undergo the treatment.

The cross-sectional view of FIG. 4 shows that the light guiding layer 58 can include a multilayer structure including layers 60-72. Layers 60-72 can be formed of any suitable type of transparent material. For example, any of the aforementioned fluoropolymers are suitable for use as layers 60-72. In addition, any of the aforementioned highly transparent materials such as, for example, polylactide (PLA), fused silica, sapphire, THE, and/or the like can be used with layers 60-72. Furthermore, each of the layers 60-72 can have a thickness, which is sufficiently thin to provide a desired level of transparency.

The layers 62, 66 and 70 of the light guiding layer can be filled with a transparent fluid. For example, in one embodiment, the layers 62, 70 can be filled with a transparent gas while the layer 66 can be filled with a transparent liquid. In an embodiment, the gas in the layers 62, 70 can have a low refractive index (e.g., at most ninety percent of the refractive index of the material forming the adjacent layers 60, 64, 68, 72), such as ambient air. In an embodiment, the liquid in the layer 66 can be substantially transparent to ultraviolet radiation. In this case, the liquid has a transparency at least similar (e.g., within ten percent) to the transparency of purified water for light wavelengths in the range of 240 nanometers to 360 nanometers. In an embodiment, the liquid in the layer 66 can be purified water as defined by the U.S. Food and Drug Administration. Alternatively, the liquid can be water sufficiently clean for human consumption (potable water).

For a layer 62, 70 including a gas, the light guiding layer 58 can further include a corresponding set of pillars 74, 76. The pillars 74, 76 also can be formed of a fluoropolymer-based material described herein. The pillars 74, 76 can be configured to maintain a shape of the corresponding low refractive index guiding layer 62, 70, respectively. To this extent, the pillars 74, 76 can be located in any pattern/random arrangement and can have any combination of one or more sizes and/or shapes, which is suitable for providing a desired amount of support. While not shown, it is understood that any fluid-filled layer, such as the layer 66, can include a set of pillars. In an embodiment, the pillars 74, 76 can comprise diffusive elements 78. In this case, as illustrated, the diffusive elements 78 can start at one layer, such as the layer 60, extend through a layer 62, and end at another layer 64. When both sets of pillars 74, 76 are included, the pillars 74 can be staggered in relation to the pillars 76.

As illustrated in FIG. 4, the ultraviolet radiation source 24 can be coupled to the light guiding layer 58 at a location adjacent to a side of the light guiding layer 58. A coupling mechanism 80 can be used to attach the ultraviolet radiation source 24 to the light guiding layer 58 and can be configured to hold the ultraviolet radiation source 24 in a position such that light enters the light guiding layer 58 at an angle optimal for wave guiding, e.g., at an angle larger than the total internal reflection angle for the light guiding layer 58. In an embodiment, at least thirty percent of the light generated by the ultraviolet radiation source 24 is guided along the layer 66. In an embodiment, the coupling mechanism 80 can be a domain formed of a fluoropolymer-based material described herein, in which the ultraviolet radiation source 24 is embedded or fused thereto. While only a single ultraviolet radiation source 24 is shown, it is understood that any number of ultraviolet radiation source 24 can be coupled to the light guiding layer 58 in any of various possible combinations of locations.

The diffusive elements 78 can be configured to allow light to propagate through an emission surface 82 out of the light guiding layer 58 in a diffusive manner. For example, the layer 60 is shown in FIG. 4 as including a set of diffusive elements 78, and the layer 64 is shown including a set of diffusive elements 78. As illustrated, the diffusive elements 78 can be located on an outer surface of the layer 60 forming the emission surface 82. Embodiments of diffusive elements 78 described herein can have any of various shapes including: truncated cone, lens, sphere, pyramid, inverted truncated cone, inverted pyramid, and/or the like. Furthermore, it is understood that a set of diffusive elements 78 can include a combination of diffusive elements of two or more different shapes. The diffusive elements 78 can be formed using any solution, such as surface patterning or roughening, welding/fusing the diffusive elements 78 to the corresponding layer 60, 64, and/or the like.

Additionally, one or more of the layers 60, 64, 68, and 72 can be formed of and/or coated with a reflective material. When utilized, a reflective coating can be located over an entirety of the layer 60, 64, 68, and 72, or only a portion of the layer 60, 64, 68, and 72. Furthermore, the reflective coating can be located on either the outermost or innermost surface of the layer 60, 64, 68, and 72. In addition, the layers 60, 64, 68, 72 can be partially reflective and partially transparent and a small ultraviolet absorption. It is understood that ultraviolet absorption can be minimized, subject to other optimization parameters.

Light rays propagating within light guiding layer 58 at greater than the TIR angle can travel further while retaining a comparable intensity (due to less frequent collisions with the walls 64, 68). In an embodiment, the ultraviolet radiation source 24 can be configured to emit light at least partially collimated in a direction of the light guiding layer 58. In this case, most of the light emitted by the ultraviolet radiation source 24 will collide with the walls 64, 68 at angles significantly larger than the TIR angle. At least partial collimation of the light emitted by the ultraviolet radiation source 24 can be achieved using any solution. For example, the emitting properties of an LED included in the ultraviolet radiation source 24 can be modified/selected to emit at least partially collimated light (e.g., a laser diode can be utilized).

FIGS. 5A-5B show illustrative light guiding layers according to other embodiments of the present invention that are suitable for use with any of the adhesive treatment devices described herein. In particular, FIG. 5A shows a light guiding layer 84 having a multi-layer structure which can include a substrate 86, an aluminum layer 88 and an AAO layer 90 having a plurality of pores 92. The substrate 86 can comprise any suitable substrate for forming an AAO layer 90 thereon. The substrate 86 can be formed of any solid material capable of supporting an aluminum layer 88 thereon. For formation of the AAO layer 90, the aluminum layer 88 can be accessible to an electrode. The light guiding layer 84 can further include a transparent film 94 (e.g., a fluoropolymer film) formed on an AAO layer 90 and a reflective film 96 formed on the transparent film 94. The reflective film 96 can be formed of any reflective material, such as polytetrafluoroethylene (e.g., Teflon), aluminum, polished aluminum, and/or the like, and can be uniform or non-uniform. In an embodiment, the reflective film 96 can have a reflectivity tailored to a set of desired characteristics of the light guiding layer 84. It is understood that the reflective film 96 can be partially transparent and partially reflective, while maintaining constant absorption. The absorption characteristics of the reflective film 96 can be sufficiently small to allow significant light guiding and transmission. Such changes in reflectivity of the reflective film 96 can promote uniform emission of light from an external surface of the reflective film 96.

The multi-layer structure of the light guiding layer 84 can be fabricated using any solution. For example, fabrication can include depositing a layer substantially consisting of aluminum (e.g., having a thickness of the layers 88, 90) and performing an anodizing treatment to the aluminum layer (e.g., by causing the aluminum layer to oxidize), thereby forming the AAO layer 90 including the plurality of pores 92 and a remaining aluminum layer 88 through which the pores do not extend.

Formation of the AAO layer 90 can include forming the plurality of pores 92 within the AAO layer 90 during an anodizing treatment. In an embodiment, at least some of the pores can extend through the AAO layer 90 and partially into the aluminum layer 88. In a more particular embodiment, substantially all of the pores can extend through the AAO layer 90. The attributes of the pores, including a characteristic size of the pores (e.g., average diameter), a maximum depth of the pores, a density of the pores, and/or the like, can vary depending on a particular anodization procedure utilized. For example, an electrolyte (e.g., oxalic acid, phosphoric acid, sulfuric acid, malonic acid, and/or the like) and a corresponding concentration of the electrolyte can be selected based on a planned pore size. Subsequently, the AAO layer 90 can be formed by placing an aluminum film into the selected electrolyte having the corresponding concentration, and applying a voltage potential in a range of approximately 35 Volts to approximately 45 Volts for a time period in the range of several hours.

The anodization procedure can be followed by etching the anodized aluminum oxide. For example, such etching can comprise chemical etching including: etching in chromic acid and phosphoric acid while a temperature is in the range of 65-80° C. The phosphoric acid can be in the range of 6 wt % to 7 wt % and the chromic acid can be in the range of 2 wt % to 3 wt %.

Furthermore, a second anodization can be performed by repeating a process substantially similar to or identical to the first anodization. In this case, hexagonally arranged nanoporous structures can be formed with one end blocked by the underlying substrate 86 and/or a remaining portion of the aluminum layer 88. A process time for the second anodization can be selected based on a target membrane thickness, and can range, for example, from one hour to forty-eight hours depending on the desired membrane thickness (e.g., a desired depth of the AAO pores 92).

Anodization can be preceded by electropolishing of aluminum deposited over the substrate 86, or electropolishing an aluminum substrate. The electropolishing may involve placing the aluminum in a mixture of perchloric acid and ethanol, where the ratio of respective chemicals is in the range of 1:3 to 1:5 by volume and a purity of the ethanol is in the range of 99%-99.9% and a purity of the perchloric acid is in the range of 69-72%. Subsequently, a voltage potential in a range of approximately ten volts to approximately twenty volts can be applied at a temperature less than 10° Celsius for 3 to 10 minutes depending on a target surface roughness.

FIG. 5A also shows that an ultraviolet radiation source 24 can be mounted to an edge side of the light guiding layer 84 using an ultraviolet radiation source coupling mechanism 80. In this manner, the light guiding layer 84 can be used as a light guiding structure. During operation, the AAO layer 90 can act as a light guiding layer for light propagating from the ultraviolet radiation source 24.

The ultraviolet radiation source coupling mechanism 80 and the ultraviolet radiation source 24 can be configured at a target angle in order to propagate light through the light guiding layer 84 in a predetermined direction. In an embodiment, the light propagates through the AAO layer 90 in a direction substantially parallel to a top surface of the AAO layer 90 and the aluminum layer 88. It is understood that the "a direction substantially parallel" means that the average light rays are moving in the direction. It is understood that individual light rays will be traveling in various directions. Regardless, the angle can be selected to provide maximum light guiding of light emitted by the ultraviolet radiation source 24. To this extent, the angle can be such that a majority of light emitted by the ultraviolet radiation source 24 enters the light guiding layer 84 at an angle optimal for wave guiding, e.g., at an angle larger than the total internal reflection angle for the light guiding layer 84.

Those skilled in the art will appreciate that the ultraviolet radiation source 24 can be coupled to the light guiding layer 84 at a different location than that illustrated in FIG. 5A. For example, the ultraviolet radiation source 24 can be coupled to a side surface (e.g., top) of the AAO layer 90. Furthermore, it is understood that any number of ultraviolet radiation sources 24 can be coupled to the light guiding layer 84 in any of various possible combinations of locations, and that the embodiments of the present invention are not meant to be limited to a single source at one location.

FIG. 5B shows a light guiding layer 98 in which two or more AAO layers can be used. In the embodiment illustrated in FIG. 5B, the light guiding layer 98 is shown having three AAO layers. In particular, the light guiding layer 98 includes AAO layer 90, an AAO layer 100 and an AAO layer 102 with each of these AAO layers having pores. Each AAO layer can be separated by a transparent layer 94. Each of the transparent layers 94 can be applied to the AAO layers in any of the aforementioned approaches. In an embodiment, the AAO layers 90, 100 and 102 can be fabricated to differ from each other by using one or more conditions. To this extent, the variation can result in the AAO layers 90, 100 and 102 having pores that differ in size, spacing, and/or the like. The differing pores amongst the AAO layers 90, 100 and 102 can result in a different averaged index of refraction for the AAO layers. It is understood that a solution for fabricating the light guiding layer 98 including multiple AAO layers 90, 100 and 102 can be implemented using any of various alternative processes not mentioned herein.

Stacking the AAO layers 90, 100 and 102 with each having different pore size and spacing between transparent layers 94 as illustrated in FIG. 5B results in a light guiding layer that can be configured to provide an optimal performance for a given target application. For example, the pore size and spacing of each AAO layer 90, 100 and 102 affects the optical properties of a given AAO layer (such as transmission, index of refraction, and light scattering). In an embodiment, the AAO layers 90, 100 and 102 can have pore sizes, spacing, thicknesses, and/or the like, which are selected to produce a target graded index of refraction for the light guiding layer 98. In a more particular embodiment, the AAO layer 90 can have pores having diameters in a range of 150 nm to 200 nm and separated by distances (e.g., as measured edge to edge) on the order of 400 nm, the AAO layer 100 can have pores having diameters of approximately 200 nm and separated by distances on the order of 250 nm, and the AAO layer 102 can have pores having diameters of approximately 50 nm and separated by distances slightly larger than 50 nm.

Fabrication of a light guiding structure described herein can be performed using any solution. For example, illustrative light guiding structures are shown and described in U.S. patent application Ser. Nos. 14/853,057 and 14/853,014, both of which were filed on 14 Sep. 2015 and both of which are hereby incorporated by reference. A diffusive ultraviolet source is shown and described in U.S. patent application Ser. No. 14/853,075, filed on 14 Sep. 2015, which is hereby incorporated by reference.

Although the light guiding layers of FIG. 4 and FIGS. 5A-5B show an ultraviolet radiation source 24 coupled at a side location, it is understood that the ultraviolet radiation source 24 can be coupled at a top or bottom location of the light guiding layer. In addition, the light guiding layer could have a different configuration than that illustrated in FIG. 4 and FIGS. 5A-5B. For example, a multi-layer structure of another type of light guiding layer could include a top large area, a bottom large area and four smaller side areas, with each of these areas formed from one of the aforementioned fluoropolymers or other highly transparent material. In one embodiment, the ultraviolet radiation source can be attached to the top large area of the light guiding layer, while in another embodiment, the ultraviolet radiation source can be attached to one of the side areas. Either configuration could be used to waveguide ultraviolet radiation emitted from the ultraviolet radiation source and onto a particular surface of an object.

FIGS. 6A-6D show illustrative shapes of light guiding layers that are suitable for use with the light guiding layers of FIGS. 4 and 5A-5B according to an embodiment. These shapes are illustrative of some complex shapes that can be configured to guide light (e.g., ultraviolet radiation) along a desired path, however, it is understood that other shapes are within the scope of the embodiments of the present invention, and thus the shapes illustrated in FIGS. 6A-6D are not meant to be limiting.

Figure 6B:
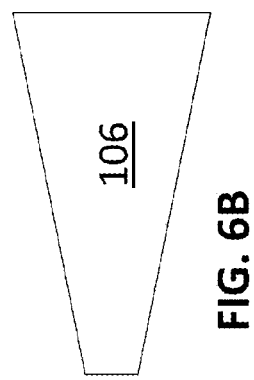
FIGS. 6A-6D show illustrative shapes of light guiding layers that are suitable for use as the light guiding layers described herein.
Figure 6D:
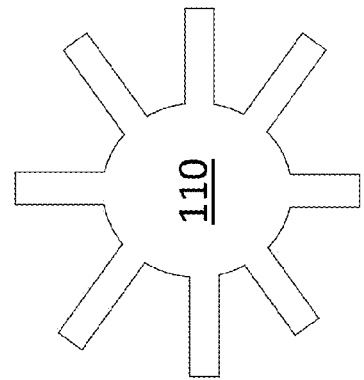
Figure 6C:
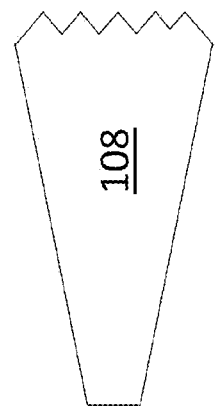
Figure 6A:
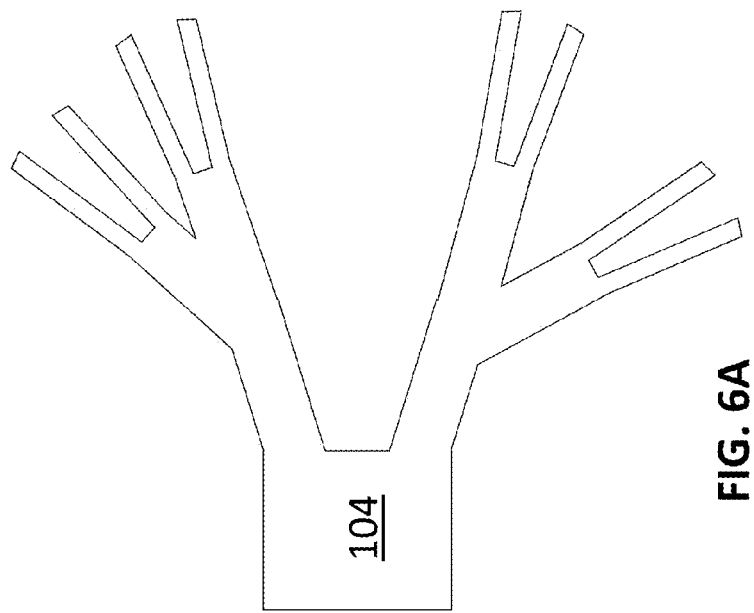

In FIG. 6A, the light guiding layer structure shape 104 includes multiple branches, and can be used to distribute radiation throughout a domain. In this case, the radiation can propagate along a path from the larger branches to the smaller branches (e.g., left to right in the drawing). Alternatively, the light guiding layer structure shape 104 can be used to combine radiation from throughout a domain, by guiding the radiation from the smaller branches to the larger branches (e.g., right to left in the drawing). In FIG. 6B, the light guiding layer structure shape 106 can be configured as a focusing element, in which case, a cross-sectional area of the light guiding layer structure shape 106 can be changed to modify a directional distribution of the propagated light. For example, the light guiding layer structure shape 106 can have a truncated inverse pyramid or cone shape, which can act as a structure for collimating radiation. As illustrated in FIG. 6C, one or more surfaces of a light guiding layer structure shape 108 described herein can contain roughness or patterning, which can provide for diffusive output of the radiation from the light guiding layer structure shape 1086C. Such roughness or patterning can be created using any solution, such as standard imprinting technology. FIG. 6D illustrates a light guiding layer structure shape 110 having a more complicated shape, which can be readily fabricated using a solution described herein.

U.S. patent application Ser. No. 14/853,057, which was filed on 14 Sep. 2015 and is hereby incorporated by reference, provides more details of light guiding layer structure shapes such as the ones illustrated in FIGS. 6A-6D including solutions for fabricating such shapes that can be configured to guide light (e.g., ultraviolet radiation) along a desired path.

FIGS. 7A-7B show illustrative adhesive treatment devices according to another embodiment of the present invention. In particular, FIGS. 7A-7B show adhesive treatment devices with an ultraviolet radiation source 24 disposed at the side of the substrate 12. In this manner, the adhesive treatment devices of FIGS. 7A-7B can deploy light guiding layers like those illustrated in FIG. 4 and FIGS. 5A-5B, and other light guiding layers that can waveguide light from a side of a treatment device as opposed to treatment devices like those illustrated in FIGS. 1A-1E, FIGS. 2A-2D, and FIGS. 3A-3B, in which light can be wave guided in a vertical direction from either a top or bottom location of the substrate.

In FIG. 7A, a treatment device 112 is shown having an ultraviolet radiation source 24 placed adjacent to the side of a light guiding layer 114. In particular, the ultraviolet radiation source 24 is placed adjacent to the side of the light guiding layer 114 such that an ultraviolet radiation source interface 116 is disposed adjacent a light guiding layer interface 118. It is understood that the ultraviolet radiation source 24 can be placed on the opposite side of the light guiding layer 114 as shown in FIG. 7A between another ultraviolet radiation source interface and a light guiding layer interface.

The light guiding layer 114 in this embodiment can include a multi-layer structure like those of FIG. 4 and FIGS. 5A-5B. In this embodiment, the light guiding layer 114 can be a multi-layer structure that includes a fluoropolymer having a transparent liquid layer 120 placed between transparent gas layers 122 with a transparent encapsulation layer 124 surrounding the transparent liquid layer 120 and the transparent gas layers 122. Any of the corresponding aforementioned materials described above with respect to FIG. 4 are suitable for use with the transparent liquid layer 120, the transparent gas layers 122, and the transparent encapsulation layer 124, as well as any of the alternatives listed thereat. In addition, any of the aforementioned highly transparent materials such as, for example, polylactide (PLA), fused silica, sapphire, THE, and/or the like, can be use in this structure of light guiding layer 112. It is understood that the multi-layer structure of FIG. 7A is illustrative of one example that can be used to facilitate the wave guiding of light in a horizontal direction through the substrate 12 and is not meant to be limiting.

In operation, light rays emitted from a side orientation of the ultraviolet radiation source 24 will propagate within the light guiding layer 114 undergoing reflection from the film boundaries. In an embodiment, the film can contain diffusive elements to allow some of the light to exit diffusively from the light guiding layer. It is understood that for some ray directions there will be a total internal reflection within a light guiding layer, but some ray directions will be allowed to exit the light guiding layer.

FIG. 7B also shows a treatment device 126 in which an ultraviolet radiation source 24 is disposed at the side of the substrate 12, but also illustrates that the ultraviolet radiation source 24 can be oriented at an angle to the side of the substrate such that the light enters a light guiding layer or wave guiding layer 128 at an angle optimal for wave guiding, e.g., at an angle larger than the total internal reflection angle for the light guiding layer 128. Although not illustrated in FIG. 7B, a coupling mechanism formed of a fluoropolymer-based material could be used to embed the ultraviolet radiation source 24 and attached to the light guiding layer in a manner described above such as fusion. In another embodiment, the ultraviolet radiation source 24 can be embedded within a side of the substrate 12. While only a single ultraviolet radiation source 24 is shown, it is understood that additional ultraviolet radiation sources 24 can be coupled to the side of the light guiding layer 128.

As shown in FIG. 7B, the light guiding layer 128 can be formed from multiple parts. In particular, the light guiding layer 128 can include a first light guiding layer part 130 and a second light guiding layer part 132 each having a multi-layer structure that are separated by an interface gap 133. In this embodiment, the first light guiding layer part 130 can be a multi-layer structure that includes a fluoropolymer having a transparent liquid layer 120 placed between transparent gas layers 122 with a transparent encapsulation layer 124 surrounding the transparent liquid layer 120 and the transparent gas layers 122. The second light guiding layer part 132 can also be a multi-layer structure that includes a fluoropolymer having a transparent liquid layer 120 placed between transparent gas layers 122 with a transparent encapsulation layer 124 surrounding the transparent liquid layer 120 and the transparent gas layers 122. However, as shown in FIG. 7B, one of the transparent gas layers 122 (e.g., the top transparent gas layer) can be segmented into individual gas layers, while the other transparent gas layer (e.g., the bottom transparent gas layer) can be a continuous layer. It is understood that this configuration of FIG. 7B is only an example and those skilled in the art will appreciate that various combinations exist for having the transparent gas layers 122 segmented or continuous.

One feature of the design of the embodiment shown in FIG. 7B is to allow the attachment of an ultraviolet LED light guiding layer part 130 to a light guiding layer part 132. In an embodiment in which the treatment device 126 is used as a self-adhesive bandage, the light guiding layer part 132 can be placed on the wound first, and the light guiding layer part 130 can be attached later, removed and reattached, if needed, to provide coupling of ultraviolet LED emitted light to the light guiding layer part 132. For successful coupling the interface gap 133 can allow light to pass there through into the light guiding layer part 132 without significant reflectance at the interface gap 133.

Again, any of the corresponding aforementioned materials described above with respect to FIG. 4 are suitable for use with the transparent liquid layer 120, the transparent gas layers 122 and the transparent encapsulation layer 124, as well as any of the alternatives listed thereat. In addition, any of the aforementioned highly transparent materials such as, for example, polylactide (PLA), fused silica, sapphire, THE, and/or the like can be used for the light guiding structures of the first and second light guiding parts 130 and 132. It is understood that the multi-layer structures of the first and second light guiding parts 130 and 132 in FIG. 7B are illustrative of one example that can be used to facilitate the wave guiding of light in a horizontal direction through the substrate 12 and is not meant to be limiting.

The treatment device 126 of FIG. 7B also shows that the multi-layer structure of the first light guiding part 130 can have a reflective layer or film 134 that can function to prevent the escape of ultraviolet radiation from that part of the device 126. Examples of materials that can be used as the reflective layer or film 134 include, but are not limited to, fluoropolymer films, a highly ultraviolet reflective expanded polytetrafluoroethylene (ePTFE) membrane (e.g., GORE® Diffuse Reflector Material), and aluminum films. It is understood that these materials can also be used with a reflective layer or film applied to an opposite side of the multi-layer structure of the first light guiding part 130. In addition, it is also possible to apply a reflective layer or film 134 to at least one of the sides of the multi-layer structure of the second light guiding part 132. Furthermore, the reflective layer or film 134 does not necessarily have to be applied to an outermost surface of the multi-layer structure as shown in FIG. 7B and instead can be located on an innermost surface.

In another embodiment, although not illustrated in FIG. 7B, an adhesive surface can be applied to the substrate 12 of the treatment device 126. Use of an adhesive surface would be beneficial in an embodiment where the treatment device 126 is used as a self-adhesive bandage to treat a skin wound. Any of the aforementioned adhesive materials could be suitable for use in this embodiment.

In operation, light rays emitted from a side orientation of the ultraviolet radiation source 24 will propagate within the multi-layer structures of the first and second light guiding parts 130 and 132 in a manner that allows for the best coupling between two light guiding parts with low reflectivity from the interface gap 133.

Figure 8:
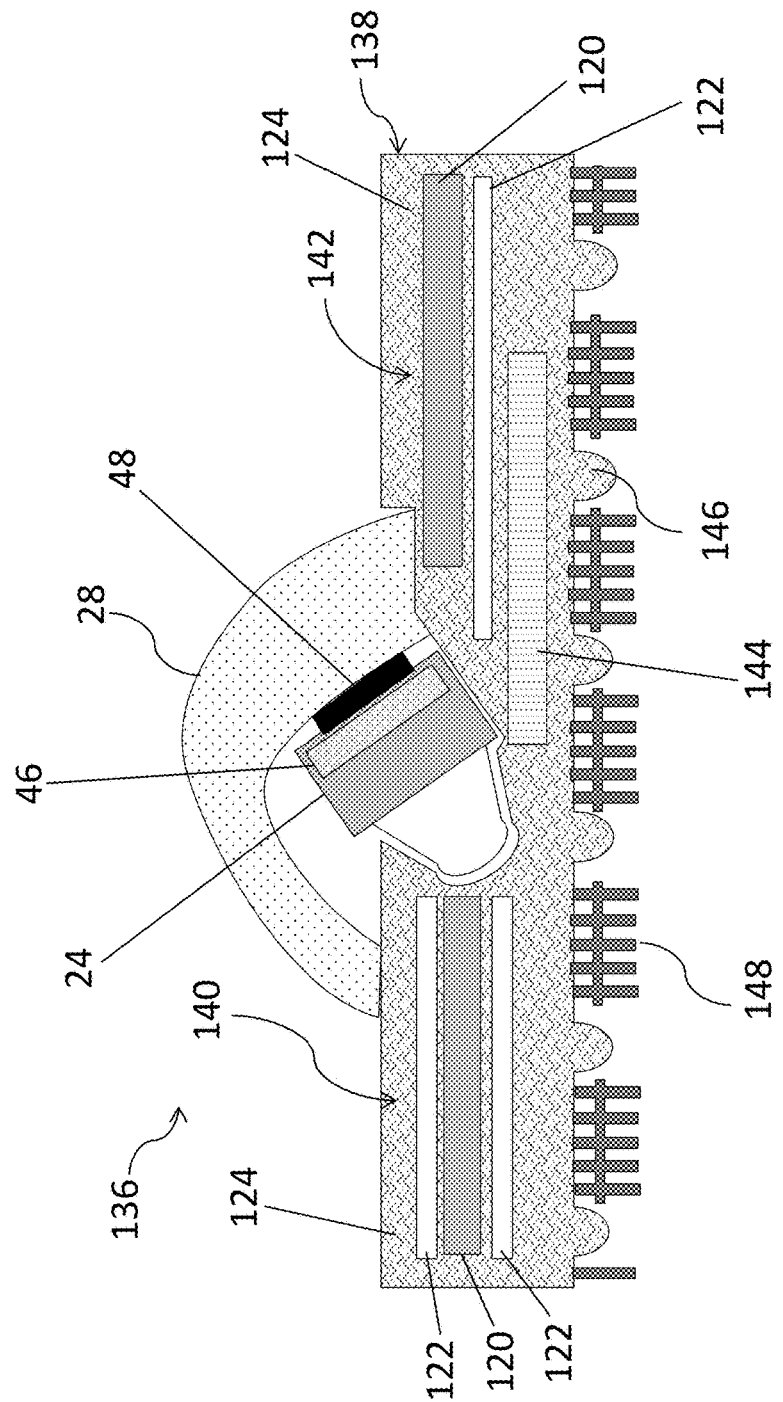
FIG. 8 shows an illustrative adhesive treatment device having a light guiding layer with a multi-layered light guiding structure according to an embodiment of the present invention.

FIG. 8 shows an adhesive treatment device 136 with a light guiding layer 138 having a multi-layer structure in a substrate 12 according to another embodiment. In this embodiment, the light guiding layer 138 can be formed from multiple parts. In particular, the light guiding layer 138 can include a first light guiding layer part 140 and a second light guiding layer part 142 each having a multi-layer structure. In this embodiment, the first light guiding layer part 140 can be a multi-layer structure that includes a fluoropolymer having a transparent liquid layer 120 placed between transparent gas layers 122 with a transparent encapsulation layer 124 surrounding the transparent liquid layer 120 and the transparent gas layers 122.

The second light guiding layer part 142 can also be a multi-layer structure that includes a fluoropolymer having a transparent gas layer 122 disposed between a transparent liquid layer 120 and a diffusive transparent layer 144 with a transparent encapsulation layer 124 surrounding the transparent liquid layer 120, the transparent gas layer 122 and the diffusive transparent layer 144. It is understood that this configuration of FIG. 8 is only an example of a multi-layer structure for the light guiding layer 138 that can be used to facilitate the wave guiding of light, and those skilled in the art will appreciate that other configurations can exist, and that the one of FIG. 8 is not meant to be limiting.

Again, any of the corresponding aforementioned materials described above with respect to FIG. 4 are suitable for use with the transparent liquid layer 120, the transparent gas layers 122 and the transparent encapsulation layer 124, as well as any of the alternatives listed thereat. In addition, any of the aforementioned highly transparent materials such as, for example, polylactide (PLA), fused silica, sapphire, THE, and/or the like can be used for the light guiding structures of the first and second light guiding parts 140 and 142.

The multi-layer structure of the light guiding layer 138 can also include diffusive elements 146 that enable light to propagate out of the light guiding layer 138 in a diffusive manner. As illustrated in FIG. 8, the diffusive elements 146 can be located on an outer surface of the light guiding layer 138 that forms an emission surface through which light propagated from the substrate 12 of the adhesive treatment device 136. Like the other elements of the multi-layer structure of the light guiding layer 138, the diffusive elements 146 can comprise any of the aforementioned fluoropolymers. The diffusive elements 146 can have any of various shapes including: a truncated cone, a lens, a sphere, a pyramid, an inverted truncated cone, an inverted pyramid, and/or the like. Furthermore, it is understood that the diffusive elements 146 can include a combination of diffusive elements of two or more different shapes. Also, the diffusive elements 146 can be formed using any solution, such as surface patterning or roughening, welding/fusing the diffusive elements 146 to the light guiding layer 138, and/or the like.

FIG. 8 also shows that the adhesive treatment device 136 can further include mesh material 148 located on a periphery of the substrate 112. In one embodiment, the mesh 148 can include a wound sanitizing absorbing mesh that is deposited on a part of the multi-layer structure of the light guiding layer 138. In particular, the mesh 148 is interspersed between the diffusive elements 146 such that the diffusive elements protrude through the mesh. In this manner, the mesh 148 can be applied adjacent to a skin wound such that the mesh touches the wound and delivers a sanitizing action, while the ultraviolet radiation source 24 can deliver a treatment to the skin wound via the multi-layer structure of the light guiding layer 138. In one embodiment, the mesh 148 can be configured with antibacterial chemicals and medicinal ointment such as antibiotic jelly or the like, to provide a treatment to the skin wound that acts in conjunction with the treatment provided by the ultraviolet radiation source 24.

FIG. 8 shows that in one embodiment the ultraviolet radiation source 24, which can include a control module 46 and a user input system 48, can be embedded in the substrate 12 of the adhesive treatment device 136 at an angle to the light guiding layer 138, and secured in place by the fastener 28. In this manner, the ultraviolet radiation source 24 can promote wave guiding, by allowing the majority of light emitted from the source to undergo total internal reflection at the interface between the diffusive elements 146 of the multi-layer structure of the light guiding layer 138 and the mesh 148 with the skin wound. It is understood that any of the other aforementioned approaches can be used to couple the ultraviolet radiation source 24 with the adhesive treatment device 136. For example, the ultraviolet radiation source 24 can be inserted in a coupling port and oriented in a position to deliver the ultraviolet radiation a predetermined target angle.

Figure 9A:
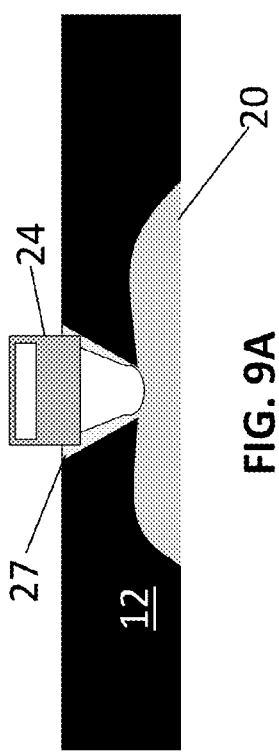
Figure 9B:
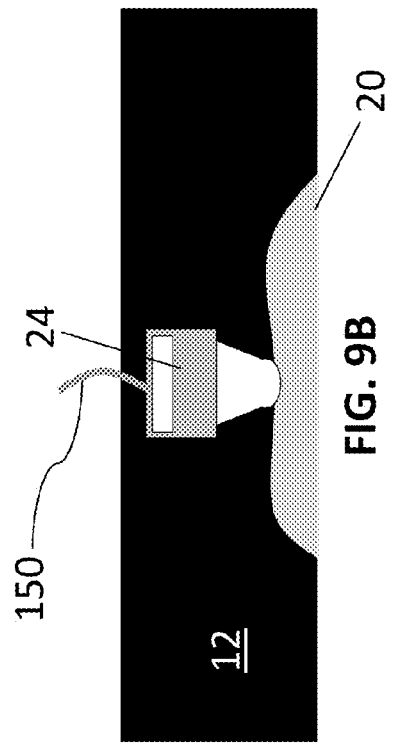
Figure 9C:
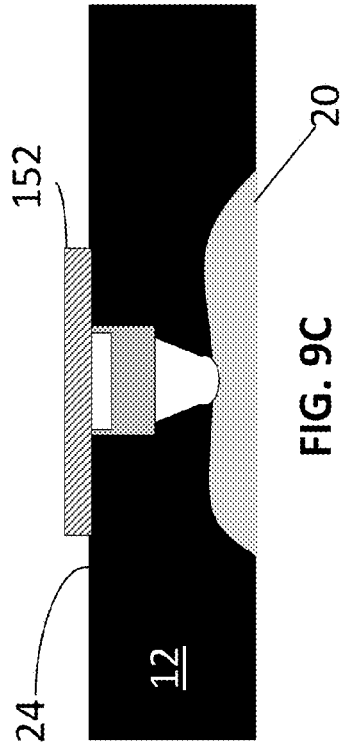

FIGS. 9A-9E show various embodiments each illustrating how the substrate 12 and ultraviolet radiation source 24 can be combined to operate within a treatment device. In FIG. 9A, the ultraviolet transparent region 20 is embedded into the substrate 12, while the ultraviolet radiation source 24 can be inserted in the opening 27 to attain access to the ultraviolet transparent region 20. FIG. 9B shows an embodiment where the ultraviolet radiation source 24 is embedded in the substrate 12 proximate the ultraviolet transparent region 20 with a data and power port 150 extended from the ultraviolet radiation source 24 out of the substrate 12. FIG. 9C shows an embodiment similar to FIG. 9A, except that in this embodiment a capping layer 152 is placed over the ultraviolet radiation source 24 to eliminate ultraviolet radiation leaking from the top of the substrate 12. The capping layer 152 can include any of the aforementioned materials that can be used to prevent leakage of ultraviolet radiation from the substrate 12. Further, the capping layer 152 can be deposited, adhered, or attached over the ultraviolet radiation source 24. FIG. 9D-FIG. 9E show embodiments where the ultraviolet radiation source 24 and an optical element 44 are attached directly to the substrate 12. The embodiment of FIG. 9D differs from the embodiment of FIG. 9E in that the ultraviolet radiation source 24 is coupled to the optical element 44, whereas FIG. 9E illustrates the ultraviolet radiation source 24 embedded in the optical element 44.

Figure 10:
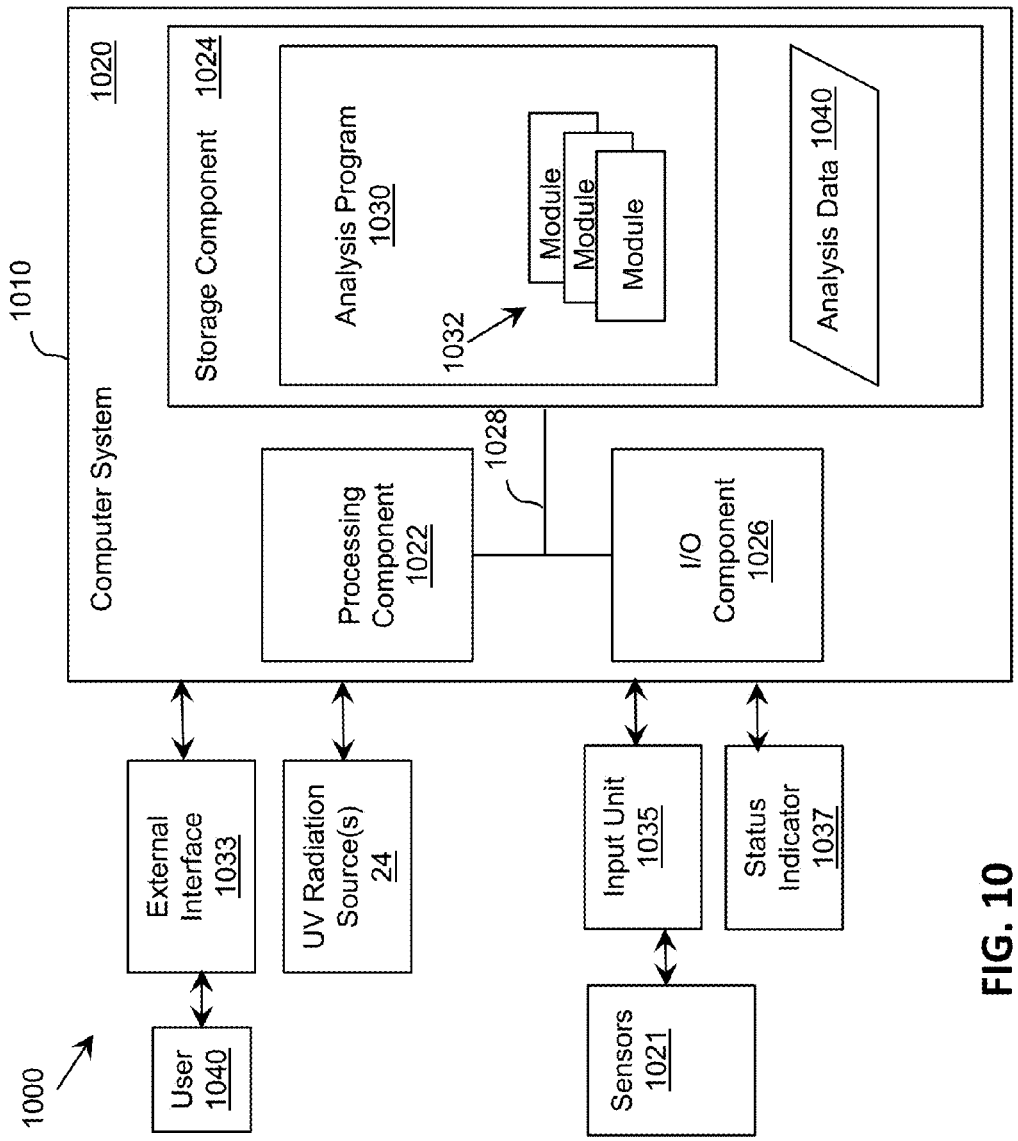
FIG. 10 shows an illustrative system for implementing an ultraviolet adhesive treatment device described herein according to one embodiment.

FIG. 10 shows an illustrative system 1000 for implementing an adhesive treatment device including an ultraviolet radiation source 24 and a control module 46 described herein according to one embodiment. The system 1000 of FIG. 10 includes a monitoring and/or control system 1010, which is implemented as a computer system 1020 including an analysis program 1030, which makes the computer system 1020 operable to manage the ultraviolet radiation source(s) 24, sensors 1021 and any other treatment sources as mentioned above. Portions of the system 1000 can be located within the control module 46 as discussed herein. In particular, the analysis program 1030 can enable the computer system 1020 to operate the ultraviolet radiation source(s) 24 to generate and direct ultraviolet radiation through the ultraviolet transparent window 22 and process data corresponding to one or more conditions detected by one or more of the sensors 1021 which are acquired by an input unit 1035.

The computer system 1020 is shown including a processing component 1022 (e.g., one or more processors), a storage component 1024 (e.g., a storage hierarchy), an input/output (I/O) component 1026 (e.g., one or more I/O interfaces and/or devices), and a communications pathway 1028. In general, the processing component 1022 executes program code, such as the analysis program 1030, which is at least partially fixed in storage component 1024. While executing program code, the processing component 1022 can process data, which can result in reading and/or writing transformed data from/to the storage component 1024 and/or the I/O component 1026 for further processing. The pathway 1028 provides a communications link between each of the components in the computer system 1020. The I/O component 1026 can comprise one or more human I/O devices, which enable a human user 1040 to interact with the computer system 1020 and/or one or more communications devices to enable a system user 1040 to communicate with the computer system 1020 using any type of communications link via an external interface 1033. To this extent, the analysis program 1030 can manage a set of interfaces (e.g., graphical user interface(s), application program interface, and/or the like) that enable human and/or system users 1040 to interact with the analysis program 1030. Furthermore, the analysis program 1030 can manage (e.g., store, retrieve, create, manipulate, organize, present, etc.) the data, such as analysis data 1040, using any solution.

In any event, the computer system 1020 can comprise one or more general purpose computing articles of manufacture (e.g., computing devices) capable of executing program code, such as the analysis program 1030, installed thereon. As used herein, it is understood that "program code" means any collection of instructions, in any language, code or notation, that cause a computing device having an information processing capability to perform a particular action either directly or after any combination of the following: (a) conversion to another language, code or notation; (b) reproduction in a different material form; and/or (c) decompression. To this extent, the analysis program 1030 can be embodied as any combination of system software and/or application software.

Furthermore, the analysis program 1030 can be implemented using a set of modules 1032. In this case, a module 1032 can enable the computer system 1020 to perform a set of tasks used by the analysis program 1030, and can be separately developed and/or implemented apart from other portions of the analysis program 1030. As used herein, the term "component" means any configuration of hardware, with or without software, which implements the functionality described in conjunction therewith using any solution, while the term "module" means program code that enables a computer system 1020 to implement the actions described in conjunction therewith using any solution. When fixed in a storage component 1024 of a computer system 1020 that includes a processing component 1022, a module is a substantial portion of a component that implements the actions. Regardless, it is understood that two or more components, modules, and/or systems may share some/all of their respective hardware and/or software. Furthermore, it is understood that some of the functionality discussed herein may not be implemented or additional functionality may be included as part of the computer system 1020.

When the computer system 1020 comprises multiple computing devices, each computing device can have only a portion of the analysis program 1030 fixed thereon (e.g., one or more modules 1032). However, it is understood that the computer system 1020 and the analysis program 1030 are only representative of various possible equivalent computer systems that may perform a process described herein. To this extent, in other embodiments, the functionality provided by the computer system 1020 and the analysis program 1030 can be at least partially implemented by one or more computing devices that include any combination of general and/or specific purpose hardware with or without program code. In each embodiment, the hardware and program code, if included, can be created using standard engineering and programming techniques, respectively.

Regardless, when the computer system 1020 includes multiple computing devices, the computing devices can communicate over any type of communications link. Furthermore, while performing a process described herein, the computer system 1020 can communicate with one or more other computer systems using any type of communications link. In either case, the communications link can comprise any combination of various types of optical fiber, wired, and/or wireless links; comprise any combination of one or more types of networks; and/or utilize any combination of various types of transmission techniques and protocols. Furthermore, the computer system 1020 can be programmed via a wireless communications solution, such as WiFi. In this embodiment, the computer system 1020 can provide reports to the user 1040 or one or more other computer systems via a wireless communications solution regarding any aspect to the illustrative environment 1000, including, but not limited to ultraviolet illumination of an object for treatment. Similarly, the computer system 1020 can generate treatment operation status information via a status indicator 1037.

While shown and described herein as an adhesive treatment device, it is understood that aspects of the present invention further provide various alternative embodiments. For example, in one embodiment, the various embodiments of the present invention provide a computer program fixed in at least one computer-readable medium, which when executed, enables a computer system to disinfect an area using ultraviolet radiation. To this extent, the computer-readable medium includes program code, such as the analysis program 1030 (FIG. 10), which enables a computer system to implement some or all of a process described herein. It is understood that the term "computer-readable medium" comprises one or more of any type of tangible medium of expression, now known or later developed, from which a copy of the program code can be perceived, reproduced, or otherwise communicated by a computing device. For example, the computer-readable medium can comprise: one or more portable storage articles of manufacture; one or more memory/storage components of a computing device; paper; and/or the like.

In another embodiment, the various embodiments of the present invention provide a method of providing a copy of program code, such as the analysis program 1030 (FIG. 10), which enables a computer system to implement some or all of a process described herein. In this case, a computer system can process a copy of the program code to generate and transmit, for reception at a second, distinct location, a set of data signals that has one or more of its characteristics set and/or changed in such a manner as to encode a copy of the program code in the set of data signals. Similarly, an embodiment of the present invention provides a method of acquiring a copy of the program code, which includes a computer system receiving the set of data signals described herein, and translating the set of data signals into a copy of the computer program fixed in at least one computer-readable medium. In either case, the set of data signals can be transmitted/received using any type of communications link.

In still another embodiment, the various embodiments of the present invention provide a method for ultraviolet illumination of an object for treatment. In this case, the generating can include configuring a computer system, such as the computer system 1020 (FIG. 10), to implement the method for ultraviolet illumination of an object for treatment. The configuring can include obtaining (e.g., creating, maintaining, purchasing, modifying, using, making available, etc.) one or more hardware components, with or without one or more software modules, and setting up the components and/or modules to implement a process described herein. To this extent, the configuring can include deploying one or more components to the computer system, which can comprise one or more of: (1) installing program code on a computing device; (2) adding one or more computing and/or I/O devices to the computer system; (3) incorporating and/or modifying the computer system to enable it to perform a process described herein; and/or the like.

The foregoing description of the various aspects of the present invention has been presented for purposes of illustration and description. It is not intended to be exhaustive or to limit the various embodiments of the present invention to the precise form disclosed, and obviously, many modifications and variations are possible. Such modifications and variations that may be apparent to an individual in the art are considered to fall within the scope of the various embodiments of the present invention.

What is claimed is:

1. A device, comprising:
    a substrate having a first side and a second side, wherein the substrate comprises a light guiding layer having a first light guiding layer part and a second light guiding layer part separated from the first light guiding layer part, the first light guiding layer part and the second light guiding layer part each having a multi-layered structure;
    an adhesive layer formed on the first side of the substrate that is configured to adhere to an object;
    an ultraviolet transparent region formed on the first side of the substrate without overlapping with the adhesive layer, wherein the ultraviolet transparent region is configured for placement adjacent to a surface of the object that is subject to undergo treatment upon the adhesive layer adhering to the object;
    an ultraviolet transparent window formed on the second side of the substrate; and
    an ultraviolet radiation source, coupled to the second side of the substrate, that is configured to emit ultraviolet radiation through the ultraviolet transparent window towards the ultraviolet transparent region and onto the surface of the subject.

2. The device of claim 1, wherein the substrate comprises ultraviolet transparent material.

3. The device of claim 2, wherein the ultraviolet transparent material comprises a transparent fluoropolymer selected from the group consisting of: EFEP, FEP, PTFE, ECTFE, PCTFE, PFA, PVDF, ETFE, THV, LDPE and MFA.

4. The device of claim 1, further comprising a removable protective pad disposed over the first side of the substrate covering the adhesive layer and the ultraviolet transparent region, wherein removal of the protective pad from the first side of the substrate exposes the adhesive layer and the ultraviolet transparent region layer for application to the surface of the object.

5. The device of claim 1, wherein the light guiding layer comprises a plurality of light diffusive elements and a mesh material formed on a periphery of the light guiding layer, wherein sections of the mesh material are interspersed between each of the plurality of light diffusive elements.

6. The device of claim 1, further comprising at least one adhesive strap attached to the second side of the substrate that is configured to secure the ultraviolet radiation source.

7. The device of claim 1, wherein the second side of the substrate includes an opening formed therein to receive the ultraviolet radiation source for placement therein at a predetermined orientation angle.

8. The device of claim 7, wherein the ultraviolet radiation source is monolithically embedded in the substrate through the opening.

9. The device of claim 1, further comprising an optical element optically coupled to the ultraviolet radiation source.

10. The device of claim 1, further comprising a control module coupled to the ultraviolet radiation source to control operation while the surface of the subject undergoes treatment.

11. The device of claim 10, further comprising a user input system coupled to the ultraviolet radiation source and the control module, wherein the user input system is configured to initiate treatment of the surface of the subject by the ultraviolet radiation source and the control module in response to receiving a user input requesting initiation of a treatment, and terminate the treatment in response to receiving a user input requesting termination of the treatment.

12. The device of claim 1, wherein the first light guiding layer part comprises a first transparent gas layer, a second transparent gas layer, and a first transparent liquid layer placed between the first transparent gas layer and the second transparent gas layer, and wherein the second light guiding layer part comprises a second transparent liquid layer, a diffusive transparent layer, and a third transparent gas layer disposed between the second transparent liquid layer and the diffusive transparent layer, and wherein a transparent encapsulation layer surrounds both the first light guiding layer part and the second light guiding layer part.

13. An adhesive treatment device, comprising:
    a substrate having a first side and a second side with an ultraviolet transparent region embedded in a volume of the substrate between the first side and the second side, wherein the ultraviolet transparent region has a surface portion that is adjacent to the first side of the substrate;
    a light guiding layer having a multi-layered light guiding structure formed in the ultraviolet transparent region, wherein the multi-layered light guiding structure includes a transparent liquid layer positioned between a first transparent gas layer and a second transparent gas layer;
    an adhesive layer formed on the first side of the substrate that is configured to adhere to an object;
    an ultraviolet radiation source coupled to the second side of the substrate that is configured to emit ultraviolet radiation through the ultraviolet transparent region towards the first side of the substrate and onto a surface of the subject that is to undergo treatment; and
    a fastener configured to fasten the ultraviolet radiation source to the substrate.

14. The adhesive treatment device of claim 13, further comprising at least one adhesive strap attached to the second side of the substrate configured to secure the ultraviolet radiation source.

15. The adhesive treatment device of claim 13, wherein the light guiding layer further comprises diffusive elements formed on the first side of the substrate, wherein the diffusive elements extend through the ultraviolet transparent region and the first side of the substrate.

16. The adhesive sterilization device of claim 13, wherein the light guiding layer is operatively coupled to the ultraviolet radiation source.

17. A self-adhesive treatment device, comprising:
- a substrate having a first side and a second side, wherein the substrate comprises a light guiding layer having a first light guiding layer part and a second light guiding layer part separated from the first light guiding layer part, the first light guiding layer part and the second light guiding layer part each having a multi-layered structure;
- an adhesive layer formed on the first side of the substrate that is configured to adhere to an object;
- an opening formed in the second side of the substrate; and
- an ultraviolet treatment system disposed in the opening that is configured to treat a surface of the object, wherein the ultraviolet treatment system comprises an ultraviolet radiation source that is configured to emit ultraviolet radiation onto the surface of the subject via the light guiding layer, wherein the ultraviolet radiation source is placed in the opening at a predetermined orientation angle to emit ultraviolet radiation onto the surface of the object at a target angle.

18. The self-adhesive treatment device of claim 17, further comprising a capping layer disposed over the ultraviolet treatment system that is configured to prevent leakage of ultraviolet radiation from the second side of the substrate.

19. The self-adhesive treatment device of claim 17, wherein the ultraviolet treatment system comprises an optical component that is configured to direct the ultraviolet radiation emitted from the ultraviolet radiation source towards the surface of the object.

20. The self-adhesive treatment device of claim 19, wherein the optical component comprises one of an ultraviolet transparent light guiding layer and a lens.

\* \* \* \* \*